United States Patent

Guillou-Bonnici et al.

(10) Patent No.: US 6,537,783 B1
(45) Date of Patent: Mar. 25, 2003

(54) PREFUNCTIONALIZED NUCLEOTIDE AND PROCESS FOR AMPLIFYING A SEQUENCE USING A PREFUNCTIONALIZED NUCLEOTIDE

(75) Inventors: Françoise Guillou-Bonnici, Villeurbanne (FR); Eric Defranc, Goncelin (FR); Antoine Hoang, Venissieux (FR); Ali Laayoun, Lyons (FR); Jean Lhomme, Meylan (FR); Emmanuelle Trevisiol, Grenoble (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/214,658

(22) PCT Filed: Aug. 1, 1997

(86) PCT No.: PCT/FR97/01445

§ 371 (c)(1),
(2), (4) Date: Jan. 11, 1999

(87) PCT Pub. No.: WO98/05766

PCT Pub. Date: Feb. 12, 1998

(30) Foreign Application Priority Data

Aug. 2, 1996 (FR) .............................................. 96 09977

(51) Int. Cl.[7] .......................... C12P 19/34; C07H 21/00
(52) U.S. Cl. .................... 435/91.1; 435/91.2; 536/22.1; 536/25.3
(58) Field of Search .......................... 435/6, 91.1, 91.2; 436/501; 536/22.1, 23.1, 24.1, 24.3–24.33, 25.3

(56) References Cited

U.S. PATENT DOCUMENTS

| 4,828,979 | A | * | 5/1989 | Klevan et al. .................. 435/6 |
| 5,399,491 | A | | 3/1995 | Kacian et al. ............ 435/91.21 |
| 5,409,818 | A | | 4/1995 | Davey et al. ............. 435/91.21 |

FOREIGN PATENT DOCUMENTS

| DE | 41 19075 | * 12/1992 |
| EP | 0 212 951 A2 | 3/1987 |
| EP | 0 231 495 A2 | 8/1987 |
| EP | 0 285 057 A2 | 10/1988 |
| EP | 0 682 121 A1 | 11/1995 |
| EP | 0 721 988 A1 | 7/1996 |
| WO | WO 91/01384 | 2/1991 |
| WO | WO 92/00989 | 1/1992 |
| WO | WO 92/20822 | 11/1992 |
| WO | WO 95/03426 | 2/1995 |

OTHER PUBLICATIONS

R.A. Jones, "Preparation of Protected Deoxyribonucleosides," *Oligonucleotide Synthesis—a practical approach*; Chapter 2, pp. 23–24 (Oct. 1984).

S. Czernecki et al. *Synthesis and Anti–HIV–1 Activity of Base Modified Analogues of 3'–Azido–2',3'–Dideoxythymidine (AZT)*, Nucleosides & Nucleotides, 12(3&4), pp. 369–380 (1993).

(List continued on next page.)

*Primary Examiner*—Ardin H. Marschel
(74) *Attorney, Agent, or Firm*—Oliff & Berridge, PLC

(57) ABSTRACT

A target nucleic acid sequence amplification method wherein at least the target nucleic acid sequence, at least one oligonucleotide primer specific for the target sequence, one or more enzymatic activities and nucleotides are provided, and the target sequence is amplified under conditions suitable in particular for said enzymatic or activity or activities, is disclosed. According to the method, at least one of the nucleotides is a prefunctionalized nucleotide that differs from the other nucleotides at least in that it includes at least one unprotected reactive covalence function in at least one predetermined site of the base of said nucleotide, in order to give a prefunctionalized amplificati product including at least one such prefunctionalized nucleotide. Nucleotides for carrying out the method are also disclosed.

23 Claims, 5 Drawing Sheets

OTHER PUBLICATIONS

M. Kurth et al., *Site–Specific Conjugation of a Radioiodinated Phenethylamine Derivative to a Monoclonal Antibody Results in Increased Radioactivity Localization in Tumor*, J. Med. Chem., 1993, 36, pp. 1255–1261.

B. R. de Costa et al., *A New Approach to the Design of a σ–2 Selective Ligands: Synthesis and Evaluation of N–[2–(3, 4–Dichlorophenyl)ethyl]–N–methyl–2–(1–pyrrolidinyl) ethylamine–Related Polyamines at σ–1 and σ–2 Receptor Subtypes*, J. Med. Chem., 1994, 37, pp. 314–321.

J. B. Hansen et al., *Partially Protected Polyamines*, Chemical Laboratory II, The H. C. Ørsted Institute, University of Copenhagen, Universitetsparken 5, DK–2100 Copenhagen, Denmark, 1982, pp. 404–405.

R. K. Bartlett, et al., *Transaminations of NN–Dimethylformamide Azine*, J. Chem. Soc., (C), 1967, 9–1664–1666.

V. Samano et al., *Efficient Conversion of 6–Aminopurines and Nucleosides into 6–Substituted Analogues via Novel 6–(1,2,4–Triazol–4–yl) purine Derivatives*[1], J. Am. Chem. Soc., 1994, 116, pp. 9331–332.

F. W. Hobbs, Jr., *Palladum–Catalyzed Synthesis of Alkynylamino Nucleosides. A Universal Linker for Nucleic Acids*, J. Org. Chem., 1989, 54, pp. 3420–3422.

J. Ludwig et al., *Rapid and Efficient Synthesis of Nucleoside 5'–O–(1–Thiotriphosphates),5'–Triphosphates and 2',3',– Cyclophosphorothioates Using 2–Chloro–4H–1,3, 2–benzodioxaphosphorin–4–one*, J. Org. Chem., 1989, 54, 631–635.

A. Laayoun et al., *Hydrolysis of 2'–Deoxypurine Nucleosides. The Effect of Substitution at the C–8 Position*, Tetrahedron Letters, vol. 35, No. 28, pp. 4989–4990, 1994.

D. Boturyn et al., *Synthesis of Fluorescent Probes for the Detection of Abasic Sites in DNA*, Tetrahedron, vol. 53, No. 15, pp. 5485–5492, 1997.

\* cited by examiner

SEQUENCE LISTING

```
<160> NUMBER OF SEQ ID NOS:   6

<210> SEQ ID NO 1
<211> LENGTH: 11
<212> TYPE: DNA
<213> ORGANISM: Artificial Sequence
<220> FEATURE:
<221> NAME/KEY: modified_base
<222> LOCATION: (6)
<223> OTHER INFORMATION: 2'-deoxy-8-(4-pentenyl)thioadenosine
<223> OTHER INFORMATION: Description of Artificial Sequence:
      polynucleotide with a modified base
```

```
<400> SEQUENCE: 1
cgcacncacg c                                                          11

<210> SEQ ID NO 2
<211> LENGTH: 11
<212> TYPE: DNA
<213> ORGANISM: Artificial Sequence
<220> FEATURE:
<221> NAME/KEY: modified_base
<222> LOCATION: (6)
<223> OTHER INFORMATION: 2'-deoxy-8-(4,5-pentanediol)thioadenosine
<223> OTHER INFORMATION: Description of Artificial Sequence:
      polynucleotide with a modified base

<400> SEQUENCE: 2
cgcacncacg c                                                          11

<210> SEQ ID NO 3
<211> LENGTH: 11
<212> TYPE: DNA
<213> ORGANISM: Artificial Sequence
<220> FEATURE:
<221> NAME/KEY: modified_base
<222> LOCATION: (6)
<223> OTHER INFORMATION: 2'-deoxy-8-(4-butanal)thioadenosine
<223> OTHER INFORMATION: Description of Artificial Sequence:
      polynucleotide with a modified base

<400> SEQUENCE: 3
cgcacncacg c                                                          11

<210> SEQ ID NO 4
<211> LENGTH: 29
<212> TYPE: DNA
<213> ORGANISM: Unknown Organism
<220> FEATURE:
<223> OTHER INFORMATION: Description of Unknown Organism:  standard
      primer for HIVgag

<400> SEQUENCE: 4
agtgggggga catcaagcag ccatgcaaa                                       29

<210> SEQ ID NO 5
<211> LENGTH: 54
<212> TYPE: DNA
<213> ORGANISM: Unknown Organism
<220> FEATURE:
<223> OTHER INFORMATION: Description of Unknown Organism:  primer which
      carries a sense sequence of a promoter for phage
      T7 RNA polymerase

<400> SEQUENCE: 5
aattctaata cgactcacta tagggtgcta tgtcacttcc ccttggttct ctca           54

<210> SEQ ID NO 6
<211> LENGTH: 20
<212> TYPE: DNA
<213> ORGANISM: Mycobacterium tuberculosis

<400> SEQUENCE: 6
cgggatgcat gtcttgtggt                                                 20
```

PREFUNCTIONALIZED NUCLEOTIDE AND PROCESS FOR AMPLIFYING A SEQUENCE USING A PREFUNCTIONALIZED NUCLEOTIDE

The present invention relates to a process for amplifying a sequence of a target nucleic acid.

The document EP-A-0 285 057 discloses a process for treating a nucleotide, consisting in introducing, into one of the constituent elements of said nucleotide, namely the sugar, the purine or pyrimidine base and the phosphate groups, a functional group having various uses, in particular those of labeling. The resulting nucleotide, which has thus been treated, can, according to this document, be incorporated into a polynucleotide, in particular in double-stranded form, without the double helix being destabilized by the presence of this nucleotide.

However, in this case, the functional groups which are attached to the nucleotide in accordance with this prior art exhibit a variety of phenomena, such as steric hindrance, hydrophobic interactions or complexing phenomena, which prevent the polynucleotide which has incorporated said treated nucleotide from being recognized by the majority of the enzymes which would recognize the corresponding polynucleotide into which said treated nucleotide had not been incorporated.

The document WO-A-92/00989 proposes a process which uses a protein for labeling a nucleic acid sequence, in particular for obtaining a labeled probe, by amplifying a target nucleic acid. According to this process, use is made of modified nucleotides which differ from the natural nucleotides by the presence of a reactive function, amplification is carried out in order to obtain a prefunctionalized probe, and the resulting probe is reacted, by way of the reactive functions, with a protein label. To this end, the reactive function of the modified nucleotide is a nucleophilic function which is selected from thiol functions, which may, where appropriate, be protected, and amino functions.

The drawback of this process lies in the selected label which, because of its size, with the molecular weight being of the order of several thousand, will substantially limit the rate and/or yield of the covalent coupling between said label and said function, with this problem increasing with the number of modified nucleotides which are incorporated into the probe. What is more, the label can lead to a deceleration of the reactions in which the resulting probe is involved, in particular in a hybridization.

The present invention provides an amplification process which overcomes the previously mentioned drawbacks and which, in particular, does not disrupt the incorporation of the nucleotides and, as a consequence, does not have a significant influence on the yield and/or the sensitivity in a target amplification reaction, and which, furthermore, makes it possible to obtain excellent labeling of the amplification products by avoiding label instability phenomena which were previously associated with incorporation of the label.

Thus, the present invention relates to a process for amplifying a target nucleic acid sequence, according to which:

at least the following are available: the sequence of a target nucleic acid, at least one oligonucleotide primer which is specific for the target sequence, and one or more nucleotide enzyme activities, the target sequence is amplified under nucleotides is a prefunctonalized nucleotide which differs from the other nucleotides at least by the presence of at least one covalently reactive function, which is unprotected and which is arranged in at least one predetermined site on the base of said nucleotide, in order to obtain a prefunctionalized amplification product which includes at least one said prefunctionalized nucleotide.

According to an advantageous process of the invention, this process additionally comprises the following steps:

a reagent is available which comprises a covalently antireactive function, which is specific for the reactive function of the prefunctionalized nucleotide, and a functional group, and the prefunctionalized amplification product is reacted, directly or indirectly, with the reagent in order to obtain a functionalized amplification product.

Some of the terms employed in the present description are defined below, after which the invention is explained in detail.

Nucleotide according to the invention is understood as being a natural or modified nucleotide monomer as defined below.

Thus, the nucleotide monomer can be a natural nucleic acid nucleotide whose constituent elements are a sugar, a phosphate group and a nitrogen base; the sugar is ribose in RNA and is 2'-deoxyribose in DNA; depending on whether the nucleic acid is DNA or RNA, the nitrogen base is selected from adenine, guanine, uracil, cytosine and thymine; or a nucleotide which is modified in at least one of the three constituent elements; by way of example, the modification can take place at the level of the bases, generating modified products such as inosine, methyl-5-deoxycytidine, deoxyuridine, dimethylamino-5-deoxyuridine, diamino-2,6-purine or bromo-5-deoxyuridine, and any other modified base which permits hybridization, at the level of the sugar, namely, for example, replacement of at least one deoxyribose by an analog (for example: P. E. Nielsen et al., Science, 254, 1497–1500 (1991)), at the level of the phosphate group, for example boronate, alkylphosphonate or phosphorothioate derivatives.

A protective group is understood as being the groups which are conventionally employed in the chemical synthesis of nucleosides, nucleotides and oligonucleotides (see, for example: Chemistry of Nucleosides and Nucleotides, edited by Leroy B. Townsend, Plenum Press, New York and London and Protocols for Oligonucleotides and Analogs, Synthesis and Properties, edited by Sudhir Agrawal, Humana Press, Totowa, N.J.).

A labeling functional group of the invention is a molecule which is capable of directly or indirectly generating a detectable signal. The group is, in particular, selected from radioactive isotopes, enzymes which are selected, in particular, from peroxidase, alkaline phosphatase and b-galactosidase, and those enzymes which are capable of hydrolyzing a chromogenic, fluorigenic or luminescent substrate, chromophoric, chromogenic, fluorophoric, fluorigenic or luminescent chemical compounds, nucleotide base analogs and ligands such as biotin.

When the label is unable to generate a signal directly, for example when the label is an enzyme, it is necessary to add a visualizing substance, for example a substrate which corresponds to the enzyme, with the enzyme/substrate reaction generating a detectable complex for example a chromogenic or luminescent compound. By way of example, the visualizing reagent can be ortho-phenylenediamine or 4-methylumbelliferyl phosphate.

The covalently reactive function of the prefunctionalized nucleotide and the anti-reactive function of the reagent are electrophilic and nucleophilic organic chemical functions, respectively, or vice versa.

The electrophilic organic chemical function is advantageously selected from the aldehyde, activated ester, carboxylic acid, isothiocyanate, haloacyl derivatives and sulfonyl chloride functions.

The nucleophilic organic chemical function is advantageously selected from the amino, thiol, oxyamino, hydrazine and hydrazide functions; it is preferably the alkoxyamino function.

According to one variant of the invention, the covalently reactive function of the modified nucleotide is attached to the base by way of a coupling arm and/or the covalently anti-reactive function of the reagent is attached to the functional group by way of a coupling arm.

The coupling arm is selected, in particular, from saturated or unsaturated hydrocarbon chains, which are interrupted, where appropriate, by amino, amido and oxy functions.

According to a preferred process, the covalently reactive function is the oxyamino function and the covalently anti-reactive function of the reagent is the aldehyde function, and this latter is linked to a labeling functional group such as a fluorescent or luminescent group.

Advantageously, the aldehyde function is linked to the functional group by the coupling arm —NH—CS—NH—$(CH_2)_3$—, and the functional group of the reagent is fluorescein.

The prefunctionalized nucleotide product can comprise one or more, identical or different, covalently reactive functions which are introduced by one or more nucleotides. Said covalently reactive functions can react with one or more, identical or different, reagents simultaneously or sequentially. The labeling functional groups of the functionalized product can be detected simultaneously or sequentially.

It will be understood that this labeling process can be applied to one or more prefunctionalized nucleotide products, in particular in order to differentiate prefunctionalized products which are derived from different targets.

The labeled functionalized amplification product can be detected qualitatively and/or quantitatively, in homogeneous or heterogeneous phase.

In homogeneous phase, the reagent and the prefunctionalized nucleotide product interact in the same liquid medium. In heterogeneous phase, the prefunctionalized product can be treated with the reagent before or after capture on a solid support, that is to say directly or indirectly. The capture on the solid support can be effected using known means, such as adsorption, covalency, in particular using covalently anti-reactive functions which are available on the surface of the solid support, or by means of hybridization using a polynucleotide compound.

The solid support, in all suitable forms, such as tube, cone, well, microtitration plate, sheet, chip or soluble polymer, is selected from polystyrenes, styrene-butadiene copolymers, styrene-butadiene copolymers mixed with polystyrenes, polypropylenes, polycarbonates, polystyrene-acrylonitrile copolymers and styrene-methyl methylmethacrylate copolymers, from synthetic and natural fibers, from polysaccharides and cellulose derivatives, and from glass and silicon and their derivatives.

According to preferred variants of the process of the invention,
the target nucleic acid sequence is a DNA or RNA sequence and the enzymic activities comprise RNA-dependent and/or DNA-dependent DNA polymerase activities,
the enzymic activities can additionally comprise ribonuclease H activity and DNA-dependent RNA polymerase activity in order to amplify the target nucleic acid sequence in accordance with a succession of reverse transcription, transcription and digestion reactions.

The ribonuclease H and DNA polymerase enzymic activities can be supplied by one single enzyme or else each by a different enzyme.

By way of example, the process of the invention can be employed for amplifying a target nucleic acid in a sample in accordance with techniques which are well known to the skilled person, such as PCR (polymerase chain reaction), RT-PCR (reverse transcription-polymerase chain reaction) or TMA (transcription-mediated amplification) or the NASBA (nucleic acid sequence-based amplification) technique, or any other enzymic amplification technique.

The invention also relates to a nucleotide analog or a nucleotide which is prefunctionalized and which is capable of being subjected to an enzymic treatment.

Enzymic treatment of a nucleotide analog or a nucleotide includes all the in-vivo or in-vitro reactions during which at least one enzyme, whose activity is linked to a nucleotide, is involved. Thus, it comprises all reactions which include at least one enzymic step in which a nucleotide serves as substrate for the enzyme, whether said nucleotide is transformed or not during this enzymic step; by way of example, such reactions are selected from those employed in molecular biological techniques, such as transcription, ligation, elongation and restriction and, more specifically, in amplification techniques (WINN-DEEN, Journal of Clinical Assay, Vol. 19, pp. 21–26 (1996).

Thus, the enzymes whose activities are linked to nucleotides can, in particular, be selected from the following non-exhaustive list: DNA-dependent DNA polymerases, such as the Klenow fragment of *E. coli* DNA polymerase I, Taq polymerase, the T7, T4 or T5 DNA polymerases, the a, b and g viral or cellular eukaryotic polymerases; RNA-dependent DNA polymerases, such as the AMV (avian myoblastosis virus) and MMLV (Moloney murine leukemia virus) polymerases; RNA polymerases, such as the T7, T3, SP6, N4 and PBSII RNA polymerases and *E. coli* RNA polymerase; enzymes having a nuclease activity, such as the restriction endonucleases and RNAse H; or else polyA polymerases, replicases, such as the Q-beta replicase, terminal transferases or ligases.

According to a preferred embodiment, the TMA technique for amplifying a target RNA nucleic acid sequence or amplifying a target DNA nucleic acid sequence after a reverse transcription step, with said technique being described in International Application WO 91/01384, which is hereby incorporated by reference, is chosen for applying the process of the invention.

A nucleotide analog which has been prefunctionalized in accordance with the invention corresponds to the general formula (I)

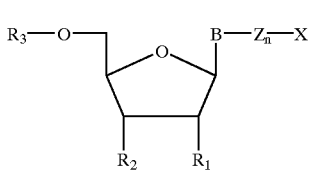

(I)

in which
B represents a nucleobase,
Z represents a coupling arm,
n is an integer equal to 0 or 1,
X represents a covalently reactive function which is attached to at least one site in the nucleobase B,
$R^1$ represents H or OH,
$R^2$ represents H, OH, a monophosphate, diphosphate or triphosphate group, or an O—R group in which R represents a protective group, $R^3$ represents H, a protective group, or a monophosphate, diphosphate or triphosphate group.

Preferably, $R^1$ and $R^2$ each represent, independently of the other, H or OH, and $R^3$ represents a monophosphate, diphosphate or triphosphate group.

A prefunctionalized nucleotide of the invention is selected from the following nucleotides:

a nucleotide whose nucleobase is derived from cytosine and contains, at least on the amino function in position 4 of the pyrimidine ring, at least one nucleophilic covalently reactive function which is unprotected and which does not have a significant influence on the enzymic treatment of said nucleotide, with the covalently reactive function being selected from the $NH_2$, $O-NH_2$, SH, hydrazine and hydrazide functions and the covalently reactive function being linked to said amino function in position 4 of the pyrimidine ring by a coupling arm which is selected from $(-CH_2-)n_1$ and $(-O-CH_2-)n_1$, in which $n_1$ is an integer of between 1 and 12; $(-CH_2-O-CH_2-)n_2$, $(-CH_2-CH_2-O-CH_2-CH_2-)n_2$, $(-CH_2-CH_2-O-CH_2-CH_2-O-CH_2-CH_2-)n_2$ and $(-CH_2-O-CH_2-CH_2-)n_2$, in which $n_2$ is an integer of between 1 and 6; and $-NH-CH_2-O-CH_2-CH_2$. Advantageously, the covalently reactive function is linked to said amino function by way of a coupling arm which is selected from $-CH_2-$, $-CH_2-CH_2-$, $-CH_2-CH_2-CH_2-$, $-CH_2-CH_2-CH_2-CH_2-$, $-CH_2-CH_2-CH_2-CH_2-CH_2-CH_2-$, $-CH_2-CH_2-O-CH_2-CH_2-$, $-CH_2-CH_2-O-CH_2-CH_2-O-CH_2-CH_2-$ and $NH-CH_2-O-CH_2-CH_2-$.

a nucleotide whose base is derived from uracil and contains, at least at position 5 of the pyrimidine ring, at least one nucleophilic covalently reactive function which is unprotected and which does not significantly influence the enzymic treatment, characterized in that the covalently reactive function is selected from the $NH_2$, $O-NH_2$, SH, hydrazine and hydrazide functions; advantageously, the covalently reactive function is linked to said amino function by way of a coupling arm which is selected from $-C\equiv C-CH_2-$, and $-C\equiv C-CH_2-NH-CO-CH_2-$, $-CH=CH-CH_2-NH-CO-CH_2-$ and $-CH=CH-CH_2$;

a nucleotide whose base is derived from adenine and contains, at least on the amino function in position 6 of the pyrimidine ring, at least one nucleophilic covalently reactive function which is unprotected and which does not have a significant influence on the enzymic treatment, characterized in that the covalently reactive function is selected from the $NH_2$, $CH_2-O-NH_2$, SH, hydrazine and hydrazide. functions; the covalently reactive function is linked to said amino function by way of a coupling arm which is selected from $(-CH_2-)n_1$ and $(-O-CH_2-)n_1$, in which $n_1$ represents an integer of between 1 and 12; $(-CH_2-O-CH_2-)n_2$, $(-CH_2-CH_2-O-CH_2-CH_2-)n_2$, $(-CH_2-CH_2-O-CH_2-CH_2-O-CH_2-CH_2-)n_2$ and $(-CH_2-O-CH_2-CH_2-)n_2$, in which $n_2$ is an integer of between 1 and 6; and $NH-CH_2-O-CH_2-CH_2$. Advantageously, the covalently reactive function is linked to said amino function by way of a coupling arm which is selected from $-CH_2-$, $-CH_2-CH_2-$, $-CH_2-CH_2-CH_2-$, $-CH_2-CH_2-CH_2-CH_2-$, $-CH_2-CH_2-CH_2-CH_2-CH_2-CH_2-$, $-CH_2-CH_2-$, $-CH_2-CH_2-O-CH_2-CH_2-$, $-CH_2-CH_2-O-CH_2-CH_2-O-CH_2-CH_2-$, and $NH-CH_2-O-CH_2-CH_2$; preferably, the coupling arm is $-CH_2-CH_2-CH_2-CH_2-$.

The invention also relates to the use of a prefunctionalized nucleotide, as previously defined, in an enzymic amplification treatment.

With regard to the enzymic treatment, the behavior of the prefunctionalized nucleotide analog or nucleotide is more or less identical to that of the corresponding nucleotide analog or nucleotide. This is because, as a result of its biological and chemical inertia with regard to enzymes, the function which is introduced into a site in the base of said analog or nucleotide does not significantly modify either the affinity or the specificity of the enzyme with regard to its substrate.

The invention finally relates to specific uses of nucleotides such as have just been defined. Preferably, they are used in amplification techniques such as those described in the following documents: EP-0 721 988, WO-95/03426, U.S. Pat. Nos. 5,409,818 and 5,399,491.

The invention will now be described in more detail by reference to the examples and attached figures, which follow and in which.

Figure 4:
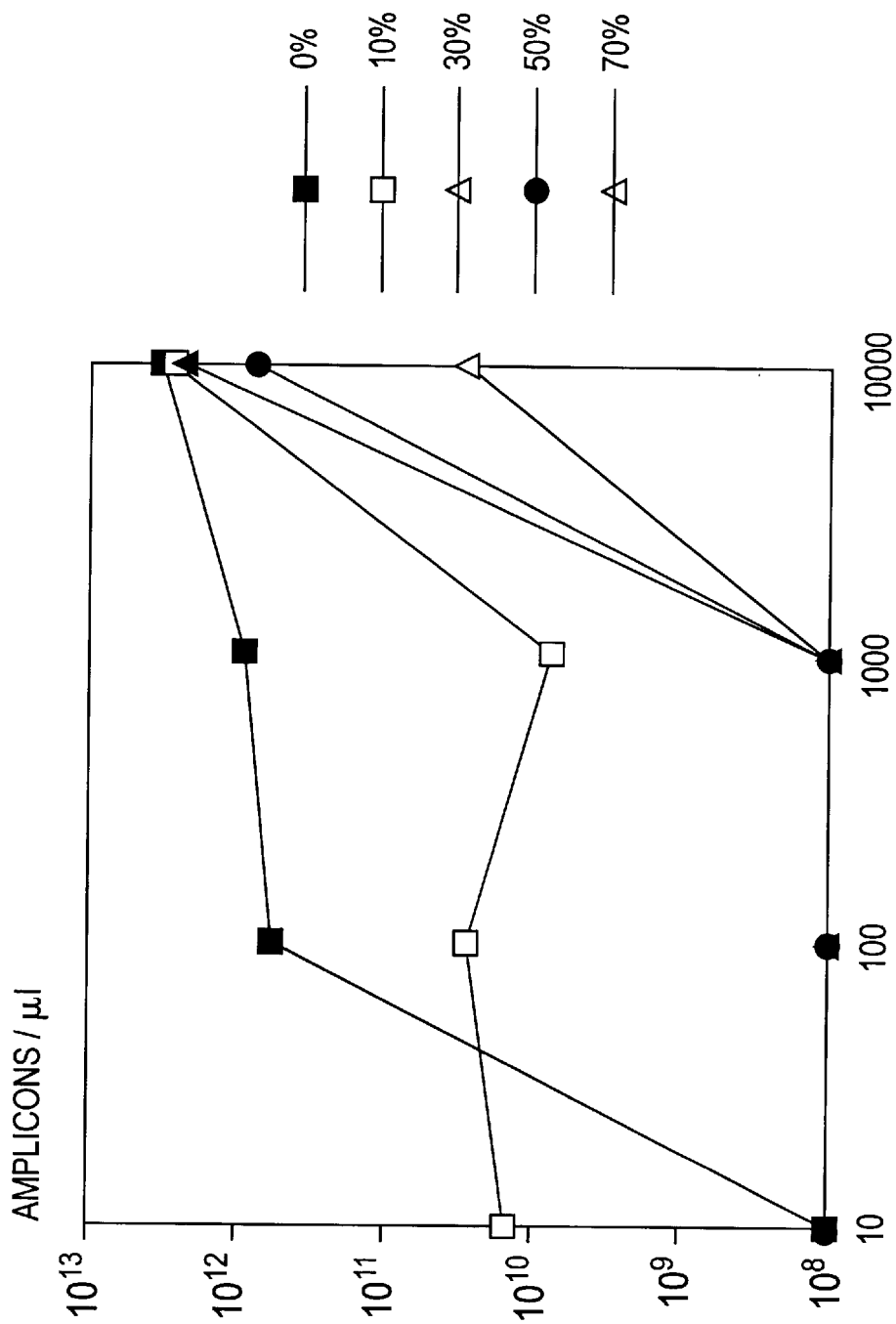
Figure 5:
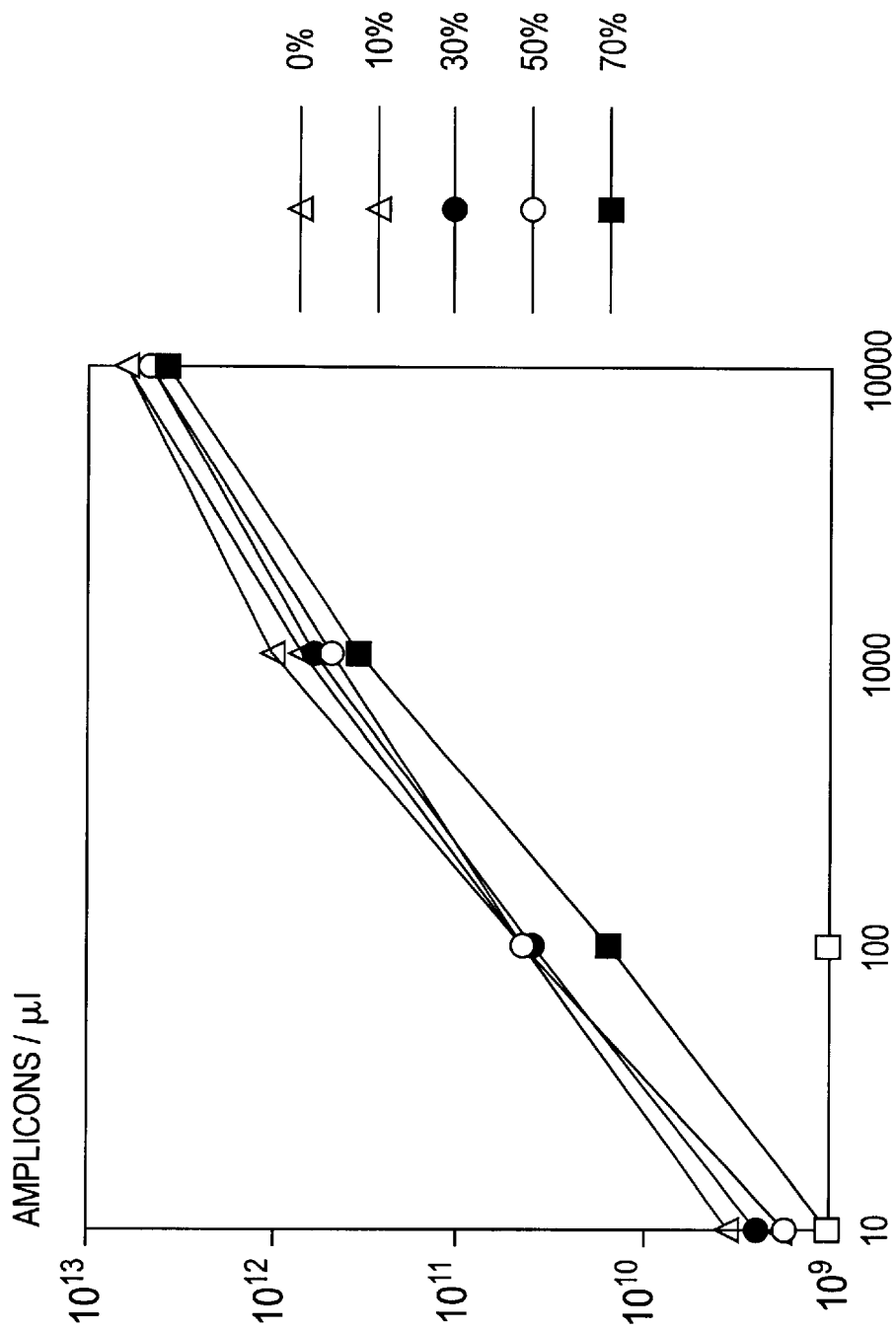

FIG. 4 demonstrates the effect of incorporating CTP-(N4)-$C_6O_2$-$NH_2$ (27a) on the sensitivity of the TMA;

FIG. 5 demonstrates the effect of incorporating CTP-(N4)-$C_4$-$NH_2$ (27b) on the sensitivity of the TMA.

In the abovementioned FIGS. 4 and 5, the number of copies of the target per reaction are given on the x axis and the number of amplicons obtained per microliter of reaction (final reaction volume=100 microliters) are given on the y axis. Specific symbols, for example ■, □, ▲, ○, ●, and a percentage, are assigned to the curves in FIGS. 4 and 5. This percentage corresponds to the percentage of the prefunctionalized nucleotide(s) as compared with the natural nucleotides in the TMA amplification reaction. FIGS. 4 and 5 show, respectively, the results of the semiquantification, by means of the ELOSA technique (described in Patent Application PCT WO 92/19812), of the number of amplicons produced from a target range of *Mycobacterium tuberculosis* 16S RNA in the presence of different ratios of 27a and 27b nucleotides as compared with their respective natural nucleotides.

While the examples which follow, and which illustrate some advantages of the invention, refer to a reagent which contains a functional group for labeling, it will of course be understood that the scope of the invention is not limited to such properties of the functional group.

Synthesis of Prefunctionalized Nucleotides and Labels

The strategy which is generally employed for prefunctionalizing nucleotides on the nucleobase consists in synthesizing protected nucleosides which carry a reactive function which is also protected. Deprotection of the hydroxyl function in the 5' position liberates the modified nucleoside, which is finally triphosphorylated in this position using the Ludwig-Eckstein method (J. Ludwig, F. Eckstein, *J. Org. Chem.*, 1989, 54, 631–635).

Hydrolysis of the groups protecting the 2' and 3' hydroxyl functions and that protecting the reactive function of the chain introduced into the base gives rise to the prefunctionalized nucleotide triphosphates.

I—Adenosine Series

EXAMPLE 1

Synthesis of the Nucleoside Having an Amino chain (4)

Route of synthesis:

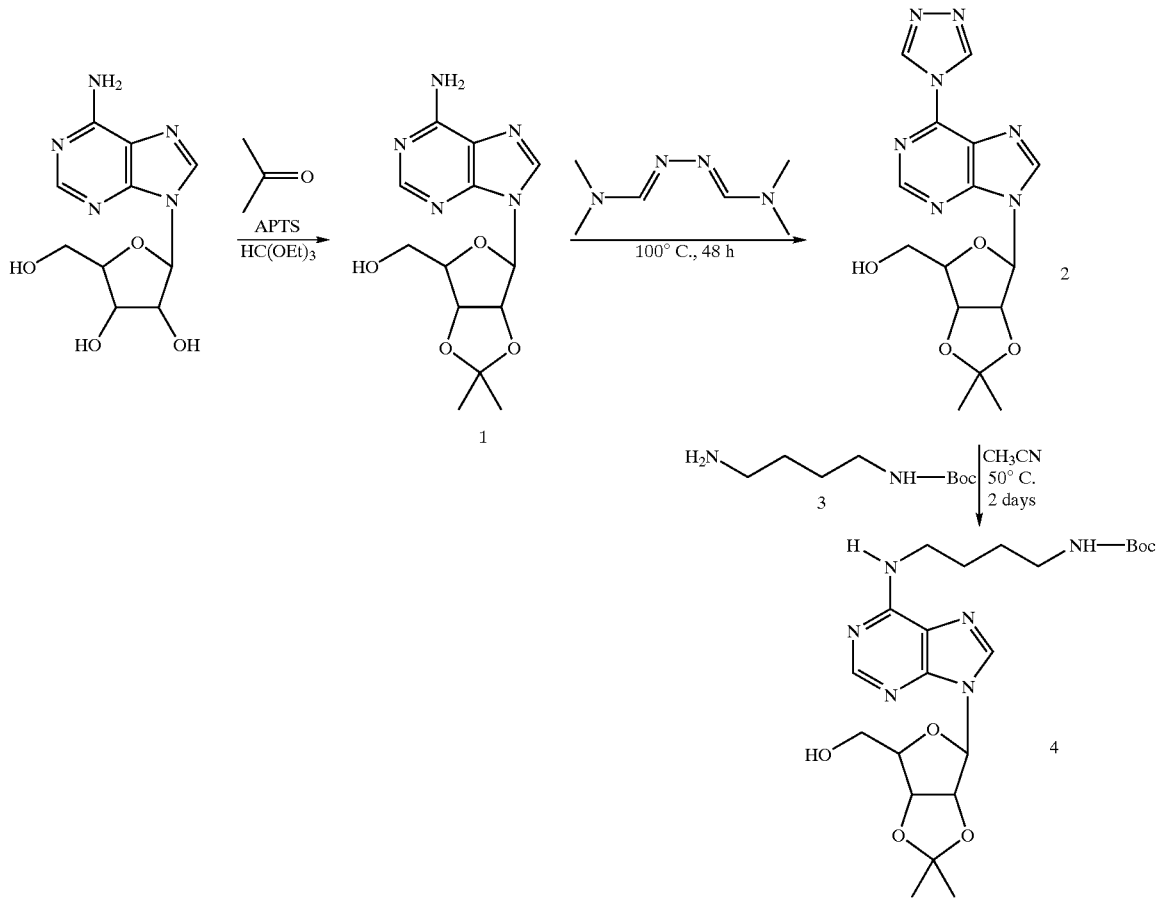

Protection and Functionalization of the Adenosine

Isopropylidene (1): (Nucleic Acid Chemistry, part 2. Townsend, Tipson, p. 768, Wiley Interscience)

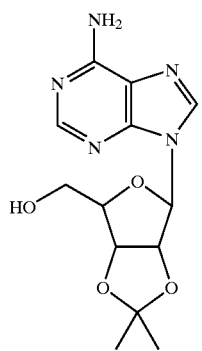

Ethyl orthoformate (12.44 ml, 74.8 mmol) is added, drop by drop, under argon, to a suspension of adenosine (5 g, 18.7 mmol, Aldrich 14659-5) in acetone (10 ml) containing APTS (3.9 g, 20.6 mmol). After reacting overnight, 110 ml of water containing 1.86 ml of 27% ammonia are then added. After stirring for 30 minutes, the reaction medium is evaporated until white crystals appear. After 12 h in a refrigerator, a white precipitate is obtained which is recrystallized in water. 4.175 g (13.5 mmol, 72%) of product (1) are obtained in the form of a white powder. This product was characterized by proton NMR.

Triazolo (2): (Samano, Miles, Robins, J. Am. Chem. Soc., 1994, 116, 9331–9332)

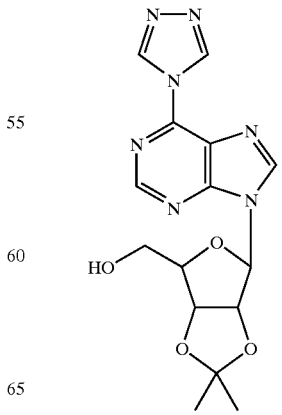

The adenosine-isopropylidene (1) (1 g, 3.2 mmol) and the amidine (1.4 g, 6.5 mmol) are stirred in pyridine (15 ml) at 100° C. for 48 h under argon. The pyridine is then evaporated and coevaporated with toluene. The oil which is obtained is then dissolved in ethyl acetate and this organic phase is washed with NaCl-saturated water. After drying over $Na_2SO_4$ and evaporating, the product (2) is obtained in the form of a white powder with a yield of 60% (700 mg, 1.9 mmol). The product 2 was characterized by mass spectrometry and proton NMR.

Synthesis of the amidine: (Bartlett and Humphreg, J. Chem. Soc., 1967, 1664–1666)

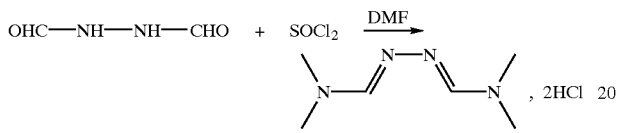

Thionyl chloride (39.96 g, 24.5 ml, 0.338 mol) is added drop by drop to N,N'-diformylhydrazine (12 g, 0.136 mol) in DMF (270 ml) at 10° C. The mixture becomes yellow. Stirring is continued for 2 days. The precipitate which is obtained is filtered and washed with DMF and then with ether. After drying in vacuo, the amidine is obtained with a yield of 95% (28 g, 0.130 mol).

Replacement of the Triazolo with the Monoprotected Diaminobutane

Monoprotection of the 1,4-diaminobutane: synthesis of (3) (Hassen, Nielsen, Ehrbar, Buchardt, Synthesis, 1982, 404–405)

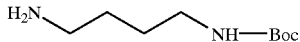

3

The solution of 1,4-diaminobutane (0.113 mol, 9.94 g, 11.4 ml) in chloroform (250 ml) is cooled down to 0° C. A solution of di-tert-butyl dicarbonate (0.022 mol, 4.95 g, 5.22 ml) in chloroform (250 ml) is then added, drop by drop, under argon. The mixture is stirred overnight at room temperature. The precipitate which has formed is filtered off and the filtrate is evaporated. The residual oil is dissolved in a saturated aqueous solution of NaCl (40 ml): the bi-protected product is thus removed by filtration. The aqueous phase is then extracted with ether (5×50 ml). The organic phases are combined, dried over $Na_2SO_4$ and evaporated. The product (3) is thus obtained in the form of an oil and with a yield of 99% (3.8 g, 0.0218 mol). The product (3) was characterized by mass spectrometry and by proton NMR.

Replacement of the Triazolo with the Diaminobutane-monoboc: Synthesis of (4)

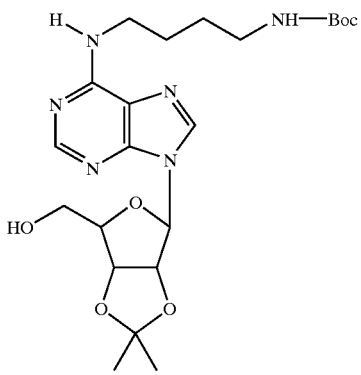

4

The product (2) (500 mg, 1.4 mol) is dissolved in 20 ml of acetonitrile. The compound (3) (1.31 g, 7 mmol) is then added. The reaction medium is heated at 50° C. for 2 days and analyzed by HPLC.

After evaporation of the acetonitrile, the residue is dissolved in ethyl acetate and this organic phase is washed with NaCl-saturated water. After drying and evaporating the ethyl acetate, the residue is chromatographed on silica gel (eluent: $CH_2Cl_2$, and then $CH_2$/MeOH, 98/2, 95/5 (v/v)). After evaporation and precipitation in hexane, the product (4) is obtained in the form of a white powder with a yield of 80% (563 mg, 1.12 mmol). The nucleoside (4) was characterized by mass spectrometry and by proton NMR.

Phosphorylation by the Eckstein method (Ludwig, Eckstein, *J. Org. Chem.*, 1989, 54, 631–635)

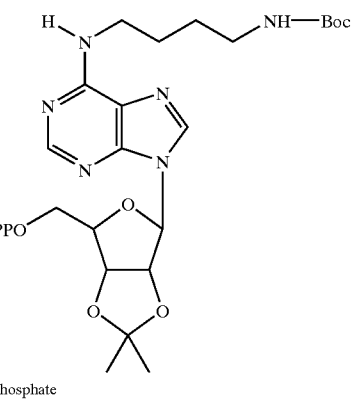

5

PPP = triphosphate

The nucleoside (4) (48 mg, 100 mmol) is dissolved in anhydrous pyridine and this solution is evaporated 2 times. 100 ml of pyridine, 300 ml of dioxane and a freshly prepared solution of 2-chloro-4H-1,2,3-dioxaphosphorin-4-one in dioxane (130 ml, 130 mmol) are then added under argon. The mixture is left to stir for 20 minutes and a 0.5 M solution of tributylammonium pyrophosphate in anhydrous DMF (320 ml) and, simultaneously, 130 ml of tributylamine are then added.

After the mixture has been stirred for 30 minutes, 2 ml of a 1% solution of iodine in a pyridine/water (98/2, v/v) mixture are added. After the mixture has been stirred for 20 minutes, the excess of iodine is destroyed with a 5% aqueous solution of $NaHSO_3$ and the stirring is continued for 10 minutes. The mixture is evaporated to dryness and a water/dichloromethane extraction is then carried out. Formation of the triphosphate is verified by HPLC (gradient: from 0 to 35% of B in 40 minutes; A=20 mM Tris-HCl, pH 7.6; B=20 mM Tris-HCl, pH 7.6+0.5 M NaCl). Retention time=35 minutes.

After the mixture has been evaporated, the residue is dissolved in water (10 ml), and 10 ml of a 50% aqueous solution of TFA are then added in order to deprotect the Boc and isopropylidene groups. After 30 minutes, the TFA is evaporated and coevaporated with water. The formation of a new product having a retention time of 19 minutes is thus observed.

EXAMPLE 2

Synthesis of the Adenosine Nucleotide Having an Oxyamino Chain

Route for Synthesizing the Chain

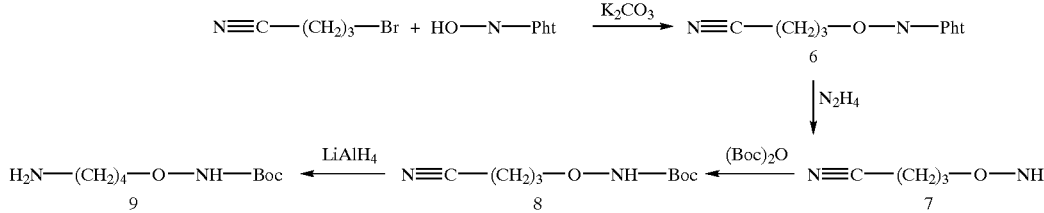

Synthesis of the Product (6)

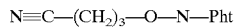

Hydroxyphthalimide (10 g, 0.061 mol) is dissolved in DMF (300 ml). $K_2CO_3$ (1.05 eq., 9 g) is then added. The formation of a precipitate is observed. After the mixture has been stirred at 50° C. for 1 h, the brominated derivative (1 eq., 9.03 g) is added and stirring is continued at 50° C. for 2 h. After filtering the mixture through cottonwool and evaporating the DMF, the residue is dissolved in ethyl acetate and the organic phase is then washed with 1N HCl, then with a 10% solution of $NaHCO_3$ and, finally, with a saturated aqueous solution of NaCl. After the organic phase has been dried and evaporated, the product (6) is obtained with a yield of 69% (9.66 g). It was characterized by proton NMR, by carbon 13 NMR and by mass spectrometry.

Hydrazinolysis: Preparation of the Chain (7)

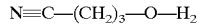

The product (6) (9.51 g, 0.041 mol) is placed in 150 ml of 95% ethanol. The addition of hydrazine (2 eq., 4 ml) leads to immediate solubilization of the initial precipitate. The formation of a white precipitate of phthalhydrazide is then observed. After reacting the mixture at 50° C. for 3 hours, it is filtered and the precipitate is washed with ethanol. After evaporation, the resulting paste is chromatographed on silica gel ($CH_2Cl_2/CH_3CN$: 9/1, v/v). Ether, and then concentrated hydrochloric acid, are added after the fractions containing the free oxyamine (7) have been evaporated. This results in the product (7) in the form of a white powder with a yield of 40% (2.30 g). It was characterized by proton NMR and carbon 13 NMR.

Protection in the Form of the Oxyamine Boc

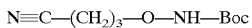

2.3 g (0.016 mol) of product (7) are dissolved in 10 ml of dioxane. A 1N aqueous solution of sodium hydroxide is then added (2 eq.: 0.032 mol. 32 ml).

Di-tert-butyl dicarbonate (1.2 eq., 0.019 mol, 4.18 g), dissolved in 20 ml of dioxane, is then added, drop by drop, in ice and under argon. After reacting the mixture at 0° C. for 3 h, the dioxane is evaporated and the pH is brought to 3 with a 1N aqueous solution of HCl; the mixture is then extracted with ether (3×50 ml). The organic phases are then washed with a 1N aqueous solution of HCl and then with a saturated aqueous solution of NaCl. After drying over $Na_2SO_4$ and evaporating, the product (8a) is obtained in the form of a yellow oil (2.56 g, 0.013 mol, 80%). It was characterized by proton NMR and carbon 13 NMR.

Reducing the Nitrile with $LiAlH_4$

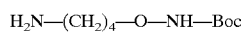

The compound (8a) (2.56 g, 0.013 mol) is dissolved in anhydrous ethyl ether (50 ml). The mixture is cooled in an ice bath. $LiAlH_4$ (3 g, 0.079 mol) is then added in three installments. Stirring is continued overnight, and water (10 ml) and a 15% aqueous solution of sodium hydroxide are then added. After the white precipitate which is thereby formed has been filtered off, the organic phase is washed with a saturated aqueous solution of NaCl. After drying over $Na_2SO_4$ and evaporating, the product 9 is obtained in the form of an oil (769 mg, 0.0037 mol, 29%). It was characterized by proton NMR and carbon 13 NMR. The chain (8b) was characterized by proton NMR and carbon 13 NMR.

Replacing the Triazolo with the Oxyamine Chain

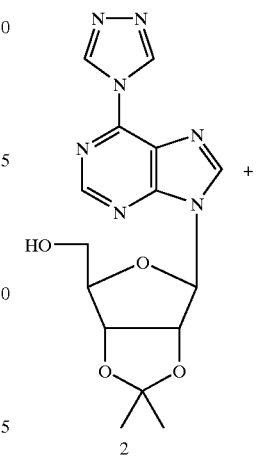

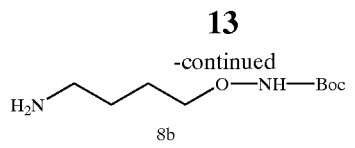

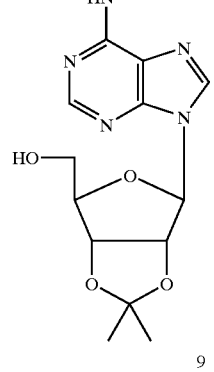

The product (2) (246 mg, 0.68 mmol) is dissolved in 20 ml of acetonitrile. The chain (8b) (700 mg, 3.43 mmol) is then added. The mixture is held at 50° C. The reaction is followed by HPLC: it develops very slowly. After a week, the solvent is evaporated. The resulting residue is dissolved in ethyl acetate and the organic phase is washed with NaCl-saturated water. Drying over $Na_2SO_4$ and evaporating results in a yellow oil, which is chromatographed on silica gel (eluent: $CH_2Cl_2$/MeOH: 97/3, v/v). After the solvent has been evaporated, the product (9) results in the form of a white powder (120 mg, 0.24 mmol, 35%). The product (9) is characterized by proton NMR and by mass spectrometry.

Phosphorylating the Nucleoside (9)

The nucleoside (9) is phosphorylated, thereby forming the nucleotide (10), using the protocol described in Example 1 (preparation of the nucleotide 5).

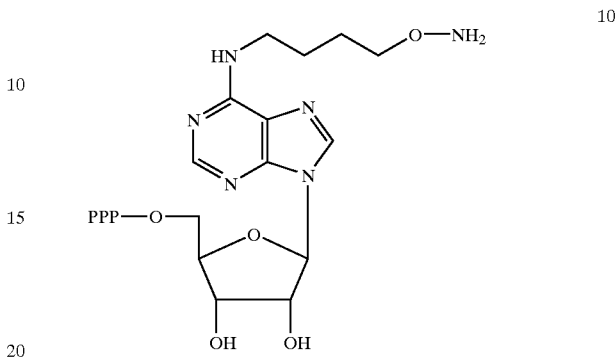

II—Uridine Series

EXAMPLE 3

Synthesis of Uridine Having an Amine Chain (15)

Route of Synthesis

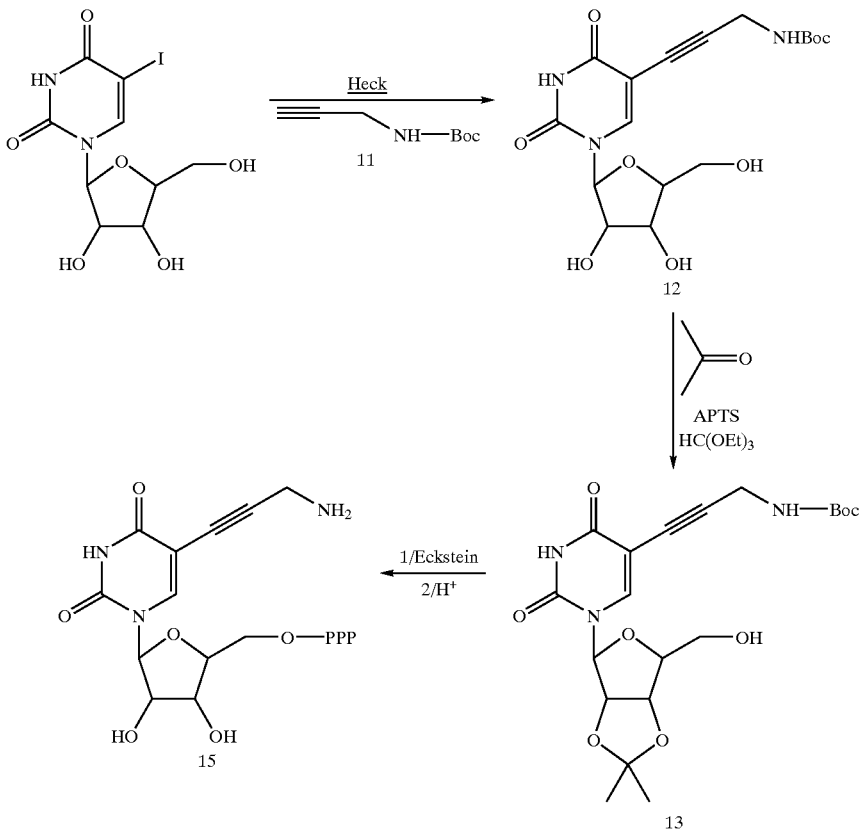

Synthesizing the Chain

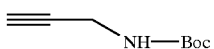
11

5 ml of propargylamine (73 mmol) are dissolved in a 1N NaOH/dioxane (146 ml/50 ml) mixture. 20 ml of Boc$_2$O dissolved in 50 ml of dioxane are then added, drop by drop, at 0° C. and under argon. The formation of a precipitate is observed. After 8 h, the precipitate of carbonate is filtered off and the pH is brought to 3 with a 1N aqueous solution of HCl; the mixture is then extracted with dichloromethane. The organic phase is subsequently washed with a saturated aqueous solution. of NaCl and then dried over Na$_2$SO$_4$ and finally evaporated. The product (11) is precipitated by adding hexane. This results in 8.92 g (0.057 mmol, 79%) being recovered. The product (11) was characterized by proton NMR and by mass spectrometry.

Introducing the chain into the base: Heck coupling (Hobbs, *J. Org. Chem.*, 1989, 54, 3420–3422).

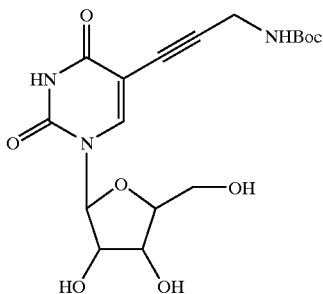
12

10 ml of DMF are degassed and placed under argon. Iodouridine (1 g, 2.56 mmol, Aldrich, 85529-7) and copper iodide (97.5 mg, 0.512 mmol) are then added. The reaction mixture is placed in the dark and triethylamine (713 ml, 518 mg, 5.12 mmol) and the Boc chain (11) (1.2 g, 7.68 mmol) are then added, still under argon. The mixture is left under argon for 10 minutes. The reaction is started by adding the tetrakis(triphenylphosphine)palladium catalyst (296 mg, 0.256 mmol). The reaction is followed by means of HPLC. After the reaction has continued overnight, the DMF is evaporated and coevaporated with acetonitrile. The resulting residue is chromatographed on silica gel (solid material loaded, eluent: CH$_2$Cl$_2$, CH$_2$Cl$_2$/MeOH: 98/2, 95/5, 90/10, 85/15-v/v). 528 mg of product (12) (1.3 mmol, 52%) are obtained after evaporation. The product (12) was characterized by proton NMR and by mass spectrometry.

Protection in isopropylidene form (Townsend, Tipson, Nucleic acid chemistry, part 2, p. 765, Wiley-interscience).

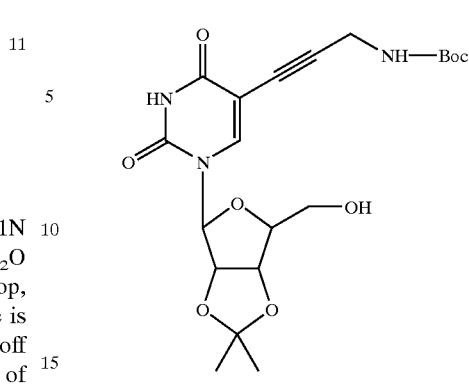
13

Ethyl orthoformate (166 ml, 148 mg, 1 mmol) is added, under argon and at ambient temperature, to a suspension of product (12) (200 mg, 0.5 mmol) in acetone (2 ml) containing APTS (9.5 mg, 0.05 mmol). The reaction is followed by means of TLC (CH$_2$Cl$_2$/MeOH 90/10). After 2 hours, dichloromethane is added and the organic phase is washed with a 10% aqueous solution of NaHCO$_3$ and then with a saturated aqueous solution of NaCl. After drying and evaporation, the product (13) is obtained in the form of a yellow powder (167 mg, 0.38 mmol, 76%).

Phosphorylating by the Eckstein method, and deprotecting ing (Ludwig, Eckstein, J. Org. Chem., 1989, 54, 631–635)

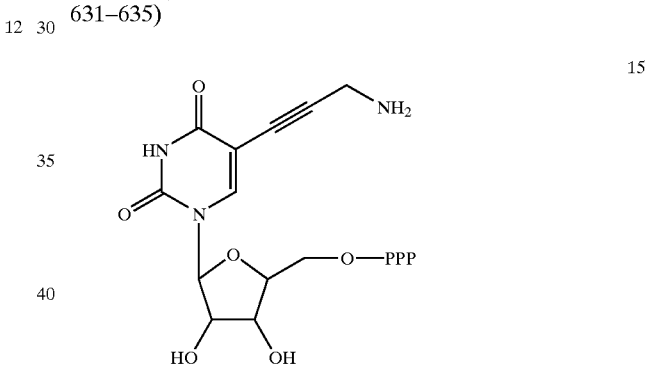
15

The nucleoside 13 (44 mg, 100 mmol) is dissolved in anhydrous pyridine and this solution is evaporated 2 times. 100 ml of pyridine, 300 ml of dioxane and a freshly prepared solution of 2-chloro-4H-1,2,3-dioxaphosphorin-4-one in dioxane (130 ml, 130 mmol) are then added under argon. The mixture is left to stir for 20 minutes and a 0.5 M solution of tributylammonium pyrophosphate in anhydrous DMF (320 ml) and, at the same time, 130 ml of tributylamine are then added.

After stirring for 30 minutes, 2 ml of a 1% solution of iodine in a pyridine/water (98/2, v/v) mixture are added. After stirring for 20 minutes, the excess of iodine is destroyed with a 5% aqueous solution of NaHSO$_3$ and the stirring is continued for 10 minutes. The mixture is evaporated to dryness and the residue is then extracted with water/dichloromethane. Formation of the triphosphate is verified by HPLC (gradient: from 0 to 35% of B in 40 minutes; A=20 mM Tris-HCl, pH 7.6; B=20 mM Tris-HCl, pH 7.6, +0.5 M NaCl). Retention time=36 minutes.

After evaporation, the residue is dissolved in water (10 ml), and 10 ml of a 50% aqueous solution of TFA are then added in order to deprotect the Boc and isopropylidene groups. After 30 minutes, the TFA is evaporated and

EXAMPLE 4

Synthesis of Uridine Having an Alkoxyamine Chain 21

Route of Synthesis

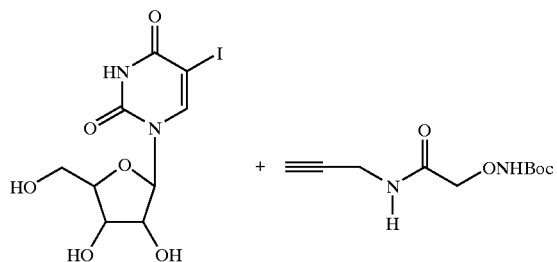

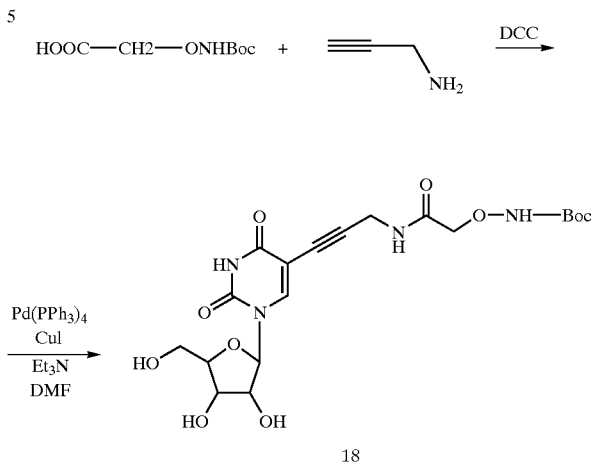

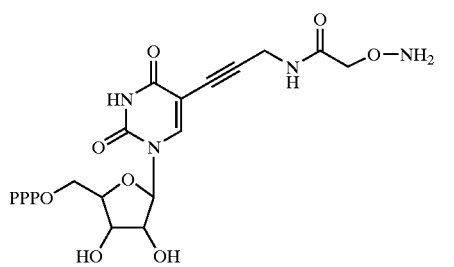

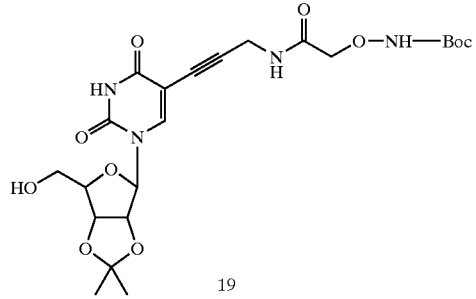

Synthesizing the carboxymethoxyamine-boc 16 (Kurth et al, *J. Med. Chem.*, 1993, 1255–1261.)

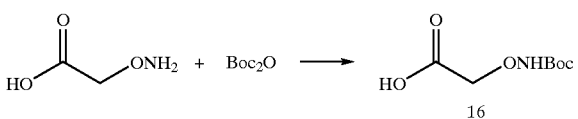

-continued

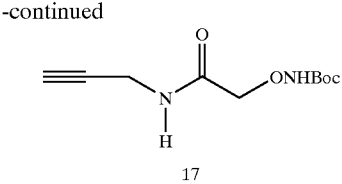

Carboxymethylamine hydrochloride (6.6 g, 60.4 mmol) is dissolved in 132 ml of water in the presence of sodium hydroxide (2 g, 50 mmol) and dioxane (66 ml). The solution is cooled down in an ice bath. Di-tert-butyl dicarbonate (13.97 g, 64.1 mmol) dissolved in dioxane (66 ml) is added dropwise. Stirring is continued overnight at ambient temperature. The reaction mixture is evaporated to dryness. 250 ml of water are added to the resulting precipitate and the whole is then extracted with ether (2×250 ml). The aqueous phase is acidified to pH 3 with 1N HCl. This phase is then extracted with ethyl ether (3×50 ml) and with ethyl acetate (3×250 ml). The organic phases are combined and dried over sodium sulfate. After evaporation, the product (16) is obtained in the form of a white powder (10 g, 52 mmol, 86%). The product (16) was characterized by proton NMR.

Synthesizing the chain by means of peptide coupling (Costa, Dominguez, Cutts, Williams, Bowen, *J. Med. Chem.*, 1994, 37, 314–321).

The product (16) (2 g, 10.4 mmol) is dissolved in freshly distilled THF. DCC (2.15 g, 10.4 mmol) is added after the medium has been cooled in ice. The mixture is stirred in the cold for 15 minutes. The propargylamine is then added. (714 ml, 10.4 mmol) Stirring is continued at ambient temperature and under argon for 2 hours. After filtering, the solvent is evaporated. The resulting residue is dissolved in dichloromethane and this solution is washed with a 1N aqueous solution of HCl, then with a 5% solution of $NaHCO_3$ and finally with a saturated aqueous solution of NaCl. After drying over $Na_2SO_4$, the dichloromethane is evaporated and the residue is chromatographed on silica gel (eluent: ethyl acetate/hexane 60/40, v/v). This results in the product (17) in the form of a white powder (1.23 g, 5.4 mmol, 52%). The product (17) was characterized by proton NMR and by mass spectrometry.

Heck coupling: Hobbs, *J. Org. Chem.*, 1989, 54, 3420–3422.

18

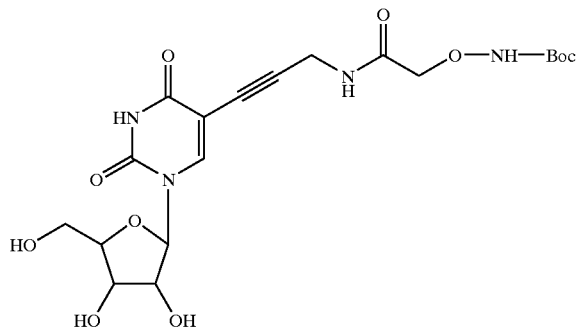

10 ml of DMF are degassed and placed under argon. Iodouridine (1 g, 2.56 mmol) and copper iodide (97.5 mg, 0.512 mmol) are then added. The reaction mixture is placed in the dark, and triethylamine (713 ml, 518 mg, 5.12 mmol) and the chain (17) (1.75 g, 7.68 mmol) are then added, still under argon. The mixture is left under argon for 10 minutes. The reaction is started by adding the tetrakis(triphenyl-phosphine)palladium catalyst (296 mg, 0.256 mmol). The reaction is followed by means of HPLC. After the reaction has continued overnight, the DMF is evaporated and coevaporated with acetonitrile. The resulting residue is dissolved in ethyl acetate and this organic phase is washed with a saturated aqueous solution of NaCl. After the evaporation of the ethyl acetate, the residue is chromatographed on silica gel (eluent: $CH_2Cl_2$/MeOH: 90/10, 85/15, 80/20, v/v). 747 mg of product (18) (1.6 mmol, 62%) are obtained after evaporation. The nucleoside (18) was characterized by proton NMR and by mass spectrometry.

Protecting in isopropylidene form (Townsend, Tipson, Nucleic acid chemistry, part 2, p. 765, Wiley-Interscience)

19

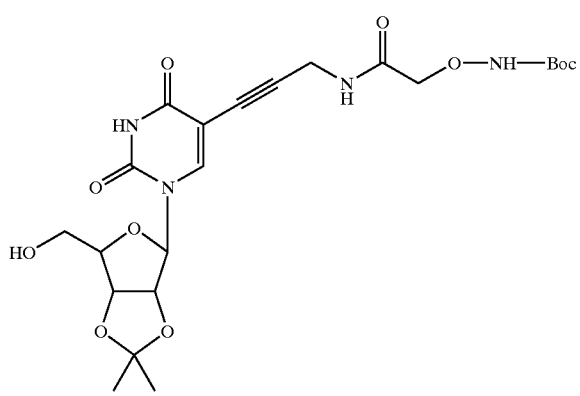

Ethyl orthoformate (355 ml, 316 mg, 2.13 mmol) is added, under argon and at ambient temperature, to a suspension of product (18) (500 mg, 1.06 mmol) in acetone (3 ml) containing APTS (20.2 mg, 0.10 mmol). The reaction is monitored by means of TLC ($CH_2Cl_2$/MeOH 90/10). After 3 hours, dichloromethane is added and the organic phase is washed with a 10% aqueous solution of $NaHCO_3$ and then with a saturated aqueous solution of NaCl. After drying and evaporating, the product (19) is obtained in the form of a yellow powder (395 mg, 0.77 mmol, 73%). The protected nucleoside (19) was characterized by proton NMR, by carbon 13 NMR and by mass spectrometry.

Phosphorylating by the Eckstein method, and deprotecting (Ludwig, Eckstein, *J. Org. Chem.*, 1989, 54, 631–635)

21

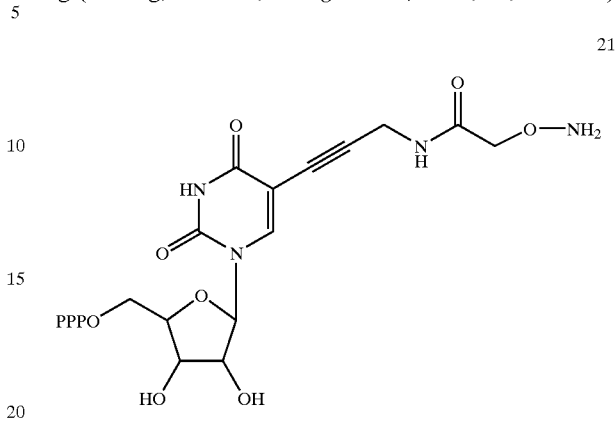

The nucleoside (19) (102 mg, 200 mmol) is dissolved in anhydrous pyridine, and this solution is evaporated 2 times. 200 ml of pyridine, 600 ml of dioxane and a freshly prepared solution of 2-chloro-4H-1,2,3-dioxaphosphorin-4-one in dioxane (260 ml, 260 mmol) are then added under argon. The mixture is left to stir for 20 minutes and a 0.5 M solution of tributylammonium pyrophosphate in anhydrous DMF (640 ml) and, at the same time, 260 ml of tributylamine are then added.

After stirring for 30 minutes, a 1% solution of iodine in a pyridine/water (98/2, v/v) mixture (4 ml, 314 mmol) is added. After stirring for 20 minutes, the excess of iodine is destroyed with a 5% aqueous solution of $NaHSO_3$ and the stirring is continued for 10 minutes. The mixture is evaporated to dryness and the residue is then extracted with water/dichloromethane. Formation of the triphosphate is verified by means of HPLC (gradient: from 0 to 35% of B in 40 minutes; A=20 mM tris-HCl, pH 7.6; B=20 mM tris-HCl, pH 7.6, +0.5 M NaCl; Waters Protein-Pak 8HR 10×100 mm DEAE column). Retention time=35 minutes.

After evaporation, the residue is dissolved in water (5 ml), and 5 ml of a 50% aqueous solution of TFA are then added in order to deprotect the Boc and isopropylidene groups. After 30 minutes, the TFA is evaporated and-coevaporated with water. This results in the formation, which is observed by HPLC, of a new product (21) having a retention time of 30 minutes. This product is purified by HPLC under the previously described conditions, and then desalted (isocratic milliQ water, Macherey Nagel C18 nucleosil column).

III—Cytidine Series

I—Synthesis of Nucleotide Triphosphates which are Modified in Position 4 by the Presence of an Alkylamino Chain In order to introduce an aminated alkyl chain in position 4 of the base, the latter was activated by introducing the tosyl group using the method of Czernecki et al. (S. Czernecki, T. Lediguarher, J. M. Valery, *Nucleosides & Nucleotides*, 1989, 54, 631–635) proceeding from [2',3'-O-isopropylidene, 5'-O-butyldimethylsilyl]uridine.

Nucleophilic replacement of the tosyl group with a diaminated alkyl chain, followed by protection of the free amino function of the introduced chain with ethyl trifluoroacetate, is carried out in one step.

Deprotection of the hydroxyl function in position 5' liberates the modified nucleoside, which is finally triphosphorylated at this position using the Ludwig-Eckstein method (J. Ludwig, F. Eckstein, *J. Org. Chem.*, 1989, 54, 631–635) described in the preceding examples.

Figure 1:
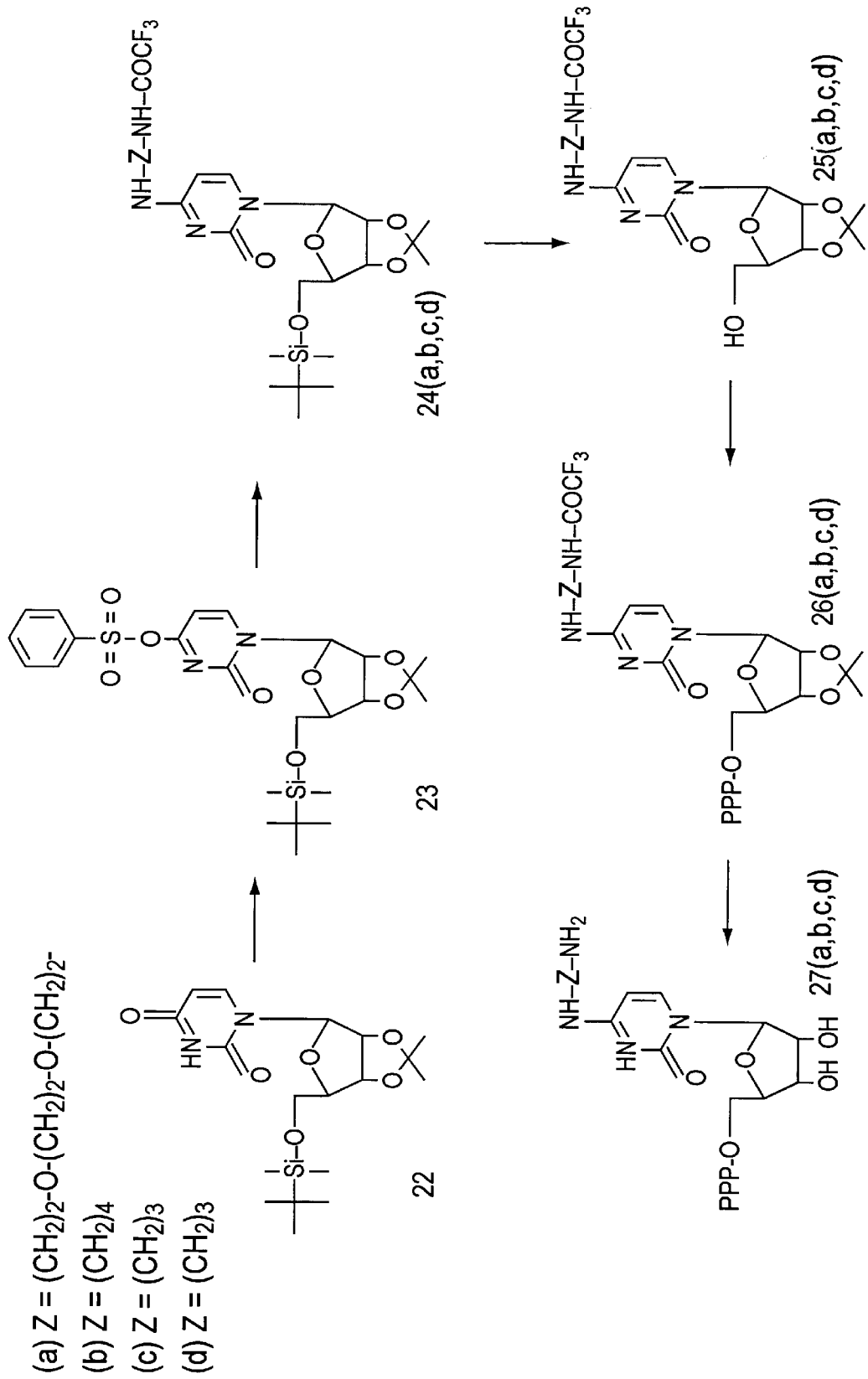
FIG. 1 depicts a general scheme for synthesizing cytidine nucleotides which carry an amino arm in position 4.

Hydrolysis of the groups protecting the 2' and 3' hydroxyl functions, and of that of the amino function of the chain introduced in the 4 position, leads to the desired nucleotide triphosphates (FIG. 1).

Figure 3:
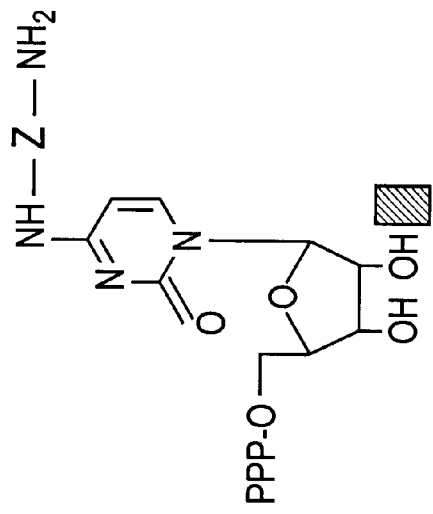
FIG. 3 depicts a scheme for synthesizing nucleotides by transamination.
Figure 3:
Figure 3:
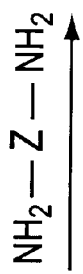
Figure 3:
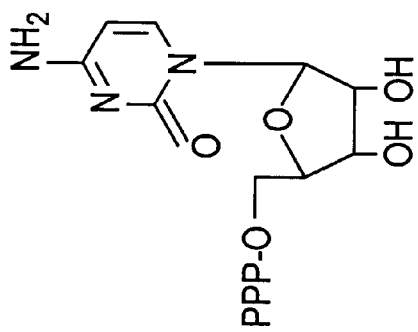

Another strategy, which consists in directly introducing the aminated chain into position 4 of the nucleotide by means of transamination, was employed for preparing the nucleotides (33) and (34) (FIG. 3).

EXAMPLE 5

Synthesis of [2',3'-o-isopropylidene, 5'-O-butyldimethylsilyl]uridine (22)

A solution of 2',3'-O-isopropylideneuridine (1 mmol, Sigma, I-5127) in pyridine (5 ml) is treated overnight, under argon and at ambient temperature, with t-butyldimethylsilyl chloride. The reaction is subsequently stopped by adding absolute ethanol (2 ml), with the mixture then being evaporated and coevaporated with toluene. The product (22) is purified by silica gel chromatography (eluent: ethyl acetate/hexane 1:1, v:v, Rf=0.3).

EXAMPLE 6

Synthesis of [2',3'-O-isopropylidene, 5'-O-t-butyldimethylsilyl-4-p-toluenesulfonyl]-uridine (23)

The compound (22) (1 mmol) in acetonitrile (17 ml) is kept refluxing, in the presence of potassium carbonate (1.3 mmol, 1.3 eq.) and p-toluenesulfonyl chloride (1.2 mmol, 1.2 eq.), for 3 hours. After the starting compound has completely disappeared, the reaction mixture is hydrolyzed at ambient temperature by adding water (2 ml) and then evaporated to dryness. The resulting residue is treated by being partitioned between ethyl acetate and water and is used as such for the following step.

TLC: Rf=0.7 (eluent: ethyl acetate/hexane 1:1, v:v). The nucleoside 23 was characterized by Proton NMR (200 Mhz, CDCl3): d=8.3 ppm (1H, d, H-6); 6.8 (2H, d, H-aroma); 7.3 (2H, d, H aroma); 6.1 (1H, d, H-5); 5.8 (1 H, s, H-1'); 4.7 (2H, s, H-2', H-3'); 4.4 (1 H, m, H-4'); 4.0–3.7 (2H, m, H-5'a, H-5'b); 2.4 (3 H, s, $CH_3$); 1.6–1.3 (2×3H, 2×s, 2×$CH_3$-isoprop); 0.8 (9H, s, 3×$CH_3$), 0.1 (6 H, s, 2×$CH_3$).

EXAMPLE 7

Synthesis of [4-N-alkyltrifluoroacetylamino-2',3'-O-isopropylidene, 5'-O-t-butyldimethylsilyl]cytidine (24)

The diaminated alkyl reagent (5 mmol, 5 eq.) is added, at ambient temperature and under argon, to a solution of (23) (1 mmol) in dichloromethane (5 ml). After stirring for 5 min, an excess of ethyl trifluoroacetate (15 mmol, 15 eq.) is added to the reaction medium and the stirring is continued for 15 min. The desired nucleoside (24) is purified by silica gel chromatography (eluent: acetone/hexane 1:2, v:v, Rf=0.2). The structure of the completely protected intermediate nucleosides (24) is confirmed by proton NMR.

Example of nucleoside (24a): NMR (200 Mhz, CDCl3), d=7.7–7.5 ppm (2H, m, H-6, NH); 5.9 (1 H, s, H-1'); 5.7 (1H, sl, NH); 5.6 (1H, d, H-5); 4.7 (2H, 1, H-2', H-3'); 4.3 (1 H, m, H-4'); 4.0–3.7 (2H, m, H-5'a, H-5'b); 3.7–3.5 (m, 12H, 6×$CH_9$); 1.6–1.3 (2×3 H, 2×1, 2×$CH_3$ isoprop); 0.8 (9H, 1, 3×$CH_3$), 0.1 (1, 6H, 2×$CH_3$).

EXAMPLE 8

Synthesis of [4-N-alkyltrifluoroacetylamino-2',3'-O-isopropylidene]cytidine (25)

The compound (24) (1 mmol), dissolved in THF (5 ml), is treated with a molar solution of tetrabutyl-ammonium fluoride (1.2 mmol, 1.2 eq.) in THF. After stirring for from 3 to 4 hours at ambient temperature and under argon, the reaction mixture is neutralized with acetic acid (1 eq.) and then evaporated to dryness. The compound (25) is purified by silica gel chromatography (eluent, acetone/hexane 1:1, v:v, Rf=0.3).

EXAMPLE 9

Synthesis of [4-N-alkyltrifluoroacetylamino-2',3'-O-isopropylidene-5'-O-triphosphate]cytidine (26)

The compound (25) (0.2 mmol) is coevaporated with pyridine (2×1 ml) and then dissolved in 400 ml of a pyridine/dioxane (1:3, v:v) mixture. A solution of dioxaphosphorinone chloride (260 µl) is added to the reaction mixture. A white precipitate forms after 5 to 10 min and, after stirring for 20 min, a solution of butylammonium pyrophosphate in DMF (0.5 M, 640 µl, 1.6 eq.) is added to the reaction mixture, followed by tributylamine (230 ml). After stirring for 30 min, the reaction mixture is oxidized with a 1% solution of iodine in the pyridine/water (98:2, v:v) (4 ml) mixture and the stirring is continued for 30 min. The excess of iodine is then destroyed with a 5% aqueous solution of sodium bisulfite and the reaction medium is evaporated to dryness. The resulting residue is dissolved in water (20 ml) and this solution is treated by washing with dichloromethane. The aqueous phase is recovered and analyzed by HPLC (millipore 5×100 mm DEAE 8 HR column, buffer A: 20 mM tris-HCl, pH 7.6, buffer B: 20 mM tris-HCl, 0.5 M NaCl, pH 7.6, flow rate: 0.5 ml/min, gradient: from 0 to 35% B in 40 min). Retention time: from 24 to 29 min. TLC: Rf=0.5, eluent:propanol:water:NH4OH (6:3:1, v:v:v)

EXAMPLE 10

Synthesis of [4-N-alkylamino-5'-O-triphosphate]cytidine (27)

Aqueous ammonia (10 ml) is added to a solution of (26) (0.2 mmol) in water (20 ml) and the mixture is stirred for 1 hour. The reaction medium is evaporated to dryness and the residue is then dissolved in water (20 ml), followed by 50% aqueous trifluoroacetic acid (10 ml), and stirring is continued for 30 min. The reaction medium is evaporated once again and then coevaporated to dryness with water. The desired compound is purified and desalted by HPLC. Analytical HPLC: retention time: 17 to 20 min. Purification: preparative 10×100 mm protein pack 8 HR DEAE column, same buffers and gradient as used in Example 9, flow-rate 2 ml/min. Desalting: RP 18 column, buffer A: water, buffer B: methanol. TLC: Rf=0.2, eluent:propanol:water:NH4OH (4:5:1, v:v:v)

II—Synthesis of Nucleotide Triphosphates which are Modified in Position 4 by the Presence of an Alkyloxy-aminated Chain An alkyl chain, which was hydroxylated at its end, was firstly introduced by nucleophilic replacement of the tosyl group in position 4 of cytidine. We then carried out a Mitsunobu reaction between the hydroxyl function of the introduced chain and N-phthalamidohydroxylamine.

Figure 2:
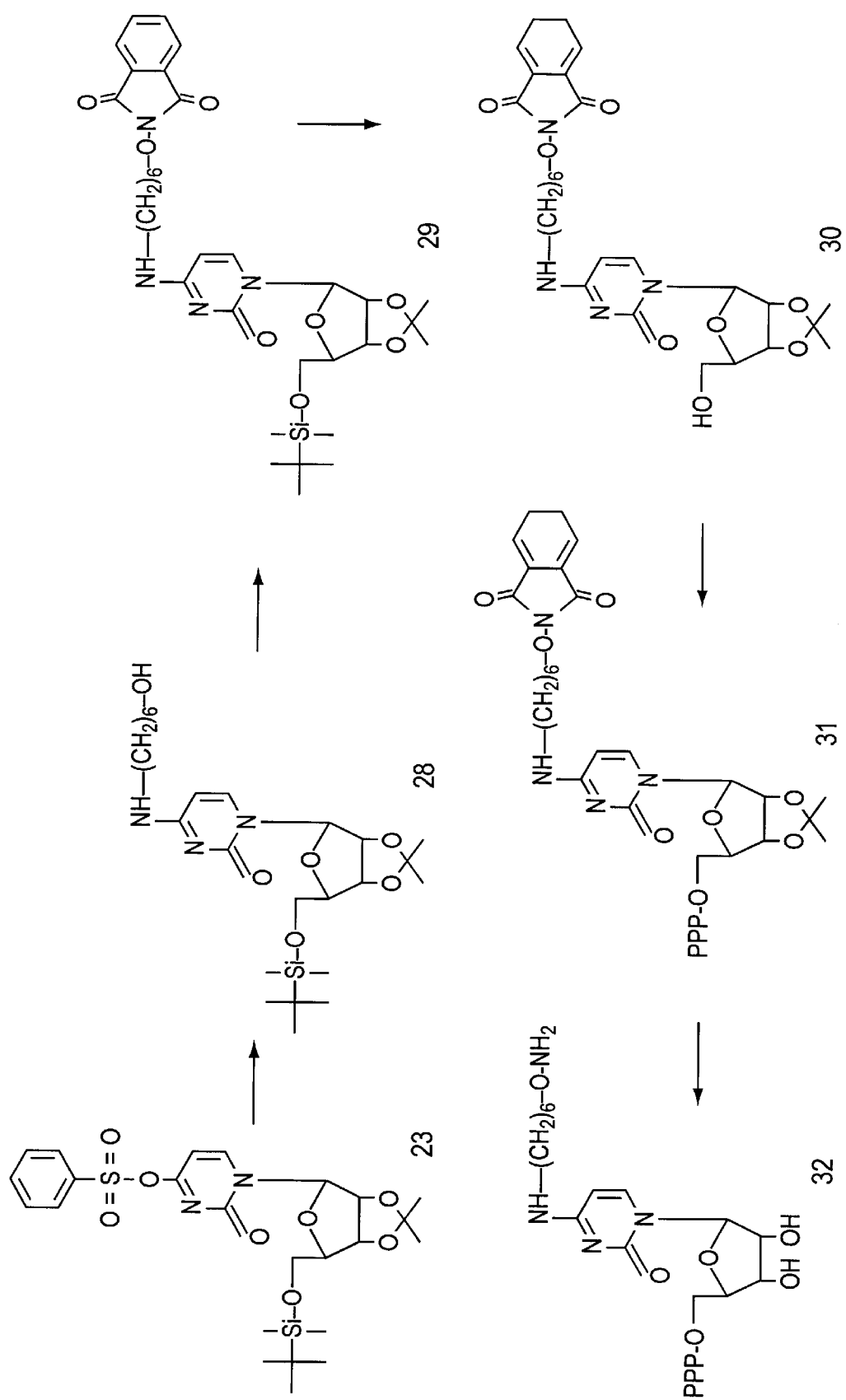
FIG. 2 depicts a scheme for synthesizing the cytidine nucleotide which carries an alkyloxyamino arm in position 4.

The corresponding alkyloxyaminated nucleotide triphosphate is obtained by following the same synthesis steps as those for the alkylaminated nucleotide triphosphates (FIG. 2).

EXAMPLE 11

Synthesis of [4-N-hexanyl-6-ol-2',3'-O-isopropylidene-5'-t-butyldimethylsilylcytidine (28).

6-Aminohexanol (5 mmol, 5 eq.) is added, at ambient temperature and under argon, to a solution of (23) (1 mmol) in dichloromethane (5 ml). After the reaction has been in progress for 30 min, the solvent is evaporated to dryness and the compound (28) is purified by silica gel chromatography.

EXAMPLE 12

Synthesis of [4-N-hexanyl-6-N-phthalamidooxyamino-2'3'-O-isopropylidene-5'-t-butyl-dimethylsilyl]cytidine (29)

Diethyl azodicarboxylate (DEAD, 3 mmol, 3 mmol, 3 eq.) is added, at ambient temperature and under argon, to a solution of (28) (1 mmol), in the presence of triphenylphosphine (3 mmol, 3 eq.) and N-phthalamidohydroxylamine (3 mmol, 3 eq.), in THF (10 ml). After stirring for an hour, the solvent is evaporated to dryness and the compound (29) is purified by silica gel chromatography.

EXAMPLE 13

Synthesis of [4-N-hexanyl-6-N-phthalamidooxyamino-2',3'-O-isopropylidene] cytidine (30)

The compound (30) was synthesized in accordance with the protocol described in Example 8.

EXAMPLE 14

Synthesis of [4-N-hexanyl-6-N-phthalamidooxyamino-2',3'-O-isopropylidene-5'-O-triphosphate]cytidine (31)

The compound (31) was synthesized in accordance with the protocol described in Example 9. Analytical HPLC (conditions as in Example 10): retention time: 44 min. TLC: Rf=0.5, eluent:propanol:water:NH4OH (6:3:1, v:v:v)

EXAMPLE 15

Synthesis of [4-N-hexanyl-6-oxyamine-5'-O-triphosphate]cytidine (32)

The totally protected nucleotide (32) is deprotected in the 2' and 3' positions with trifluoroacetic acid in accordance with the protocol described in Example 10. The alkoxyamino function is deprotected, at ambient temperature overnight, in an aqueous solution of hydrazine. The nucleotide (32) is then purified by HPLC under same conditions as those described in Example 10.

EXAMPLE 16

Synthesis of [4-N-(2,2-oxy-bis-ethylamine)-5'-O-triphosphate]cytidine (33) by Means of Transamination The cytidine triphosphate (0.1 mmol) is added to a solution consisting of sodium bisulfite (12 mmol, 120 eq.) and 2,2'-oxy-bis-ethylamine hydrochloride (7.5 mmol, 75 eq.) in water (2.5 ml) whose pH has been previously adjusted to 7.0 with a 10 M solution of sodium hydroxide; the mixture is then stirred at 37° C. for 3 days. The compound (33) is purified and desalted by means of HPLC (see HPLC conditions given in Example 10).

EXAMPLE 17

Synthesis of [4-N-(adipic acid hydrazide)-5'-O-triphosphate]cytidine (34) by Means of Transamination The nucleotide (34) was prepared by means of transamination in accordance with the protocol described in Example 16, using adipic dihydrazide (83 mg, 0.44 mol) for introducing the hydrazide function. Nucleotide (34) was also purified and desalted as described in Example 10, and its structure was confirmed by proton NMR.

IV—Functionalized Fluorophore

EXAMPLE 18

Synthesis of Fluorescein Aldehyde (36)

Route of Synthesis

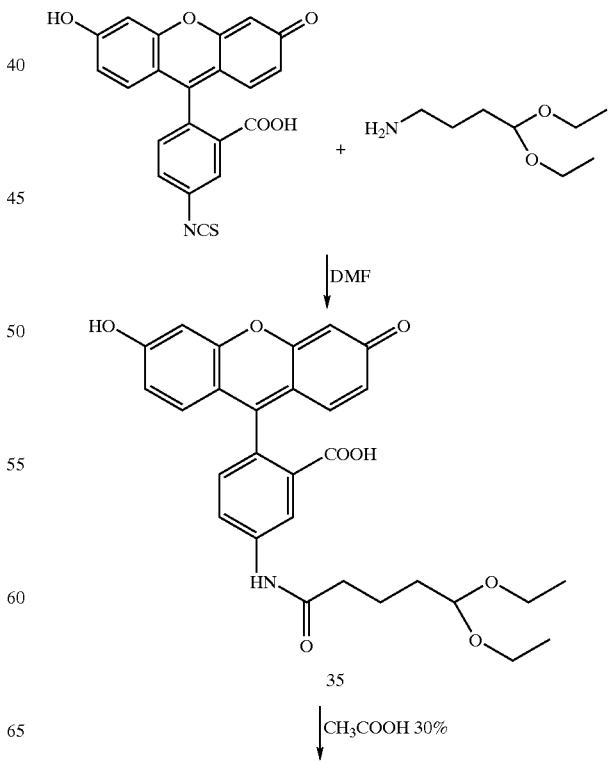

-continued

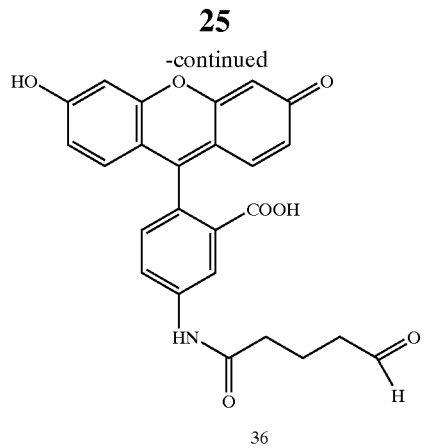

36

Coupling of the FITC to the protected aldehyde:

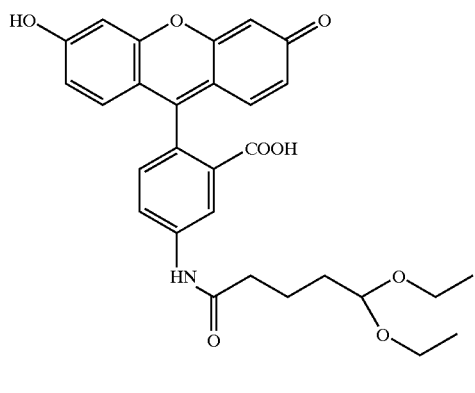

35

Fluorescein isothiocyanate (913 mg, 2.35 mmol, Aldrich, F 250-2) is dissolved, under argon, in anhydrous DMF (10 ml). Aminobutyraldehyde diethyl acetal (421 mg, 392 ml, 235 mmol) is then added. After an hour, the DMF is evaporated and the residue is chromatographed on silica gel (eluent: $CH_2Cl_2$/MeOH: 90/10, v/v). After evaporating the solvent, the product (35) is obtained in the form of an orange powder (1.21 g, 2.2 mmol, 94%). It was characterized by proton NMR and by mass spectrometry.

Deprotection of the Aldehyde

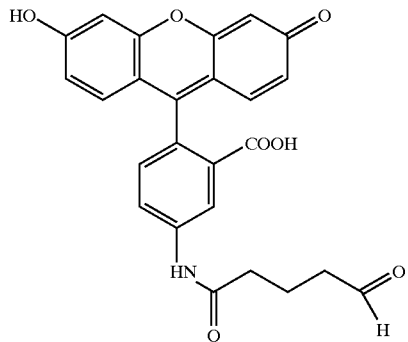

36

The protected product (35) (342 mg, 0.62 mmol) is placed in 20 ml of a 30% aqueous solution of acetic acid. After the reaction has been in progress for one hour, the solvent is evaporated and coevaporation is carried out with acetonitrile. The resulting residue is chromatographed on silica gel (eluent: $CH_2Cl_2$/MeOH: 90/10, v/v). After the solvent has been evaporated, the product (36) is obtained in the form of an orange powder (145 mg, 0.30 mmol, 48%). It was characterized by proton NMR and by mass spectrometry.

EXAMPLE 19

Chemical synthesis of a Prefunctionalized Polynucleotide

Synthesis of the starting nucleotide 2'-deoxy-8-(pentenyl)thioadenosine (38):

The starting nucleoside was synthesized using the precursor 2'-deoxy-8-mercaptoadenosine (37), which was obtained using the strategy described by A. LAAYOUN, J.-L. DECOUT and J. LHOMME in Tetrahedron Lett., 1994, 35, 4989–4990.

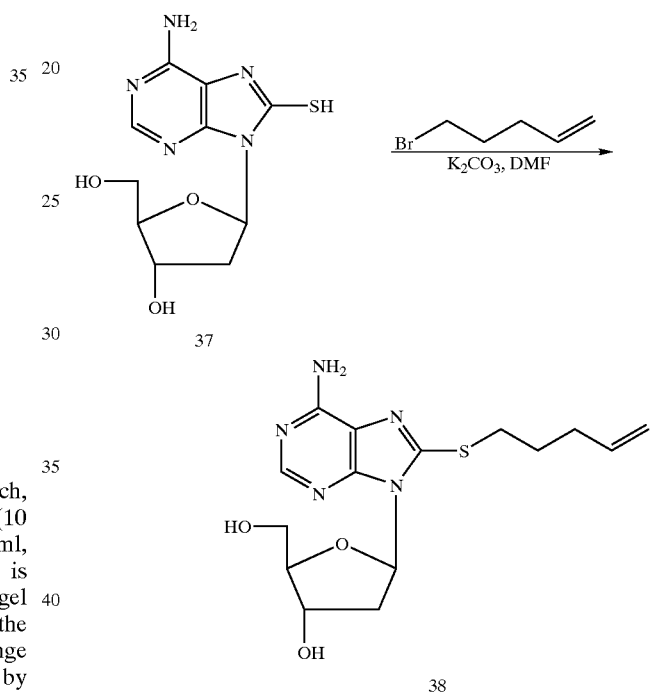

The 2'-deoxy-8-mercaptoadenosine (16.68 mmol) is dissolved in anhydrous DMF (dimethylformamide) in the presence of an excess of potassium carbonate (33.00 mmol). After adding 1-bromo-4-pentene (18.37 mmol), under argon, and incubating for 3 hours, at ambient temperature and with stirring, the mineral salts are filtered off through celite and the DMF is evaporated. A brown residue is obtained and washed with hexane and then with ethyl ether. The product is subsequently purified by chromatography on a silica column (eluent: $CH_2Cl_2$/$CH_3OH$-95/5 (v/v) and then 90/10 (v/v)). The starting nucleotide which has thus been obtained is characterized using the customary spectroscopic methods.

Chemical Synthesis of a Prefunctionalized Polynucleotide

The nucleoside which has previously been synthesized is firstly incorporated into an oligo-nucleotide. To this end, a phosphoramidite synthon (39), corresponding to the protected starting nucleoside, was prepared using the strategy described by A. J. ROGERS in "Oligonucleotide synthesis" (1984), pp. 23–34, M. J. GAIT Ed., IRL Press, Oxford.

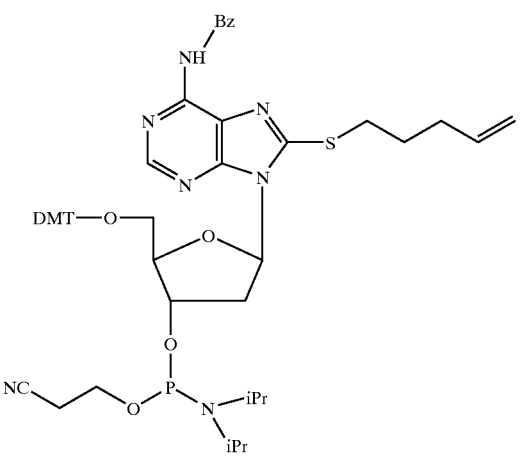

Bz = benzoyl
DMT = dimethoxytrityl

The exocyclic amino of the adenine is protected with a benzoyl group, while the 5' hydroxyl is protected with dimethoxytrityl and the 3' hydroxyl is protected with an N,N-diisopropyl-2-cyanoethylphosphor-amidite group.

The polynucleotide 5°CGCACLCACGC3' (SEQ ID NO: 1), in which L is 2'-deoxy-8-(pentenyl)thioadenosine, was synthesized by the phosphoramidite method in an automated manner on a Milligen/Biosearch 8700 appliance using the protocol suggested by the manufacturer.

The synthesized polynucleotide is purified by reverse-phase HPLC (semi-preparative Macherey Nagel 10 mm×25 cm column; C18; 5 µm porosity; eluent: 20 min gradient of from 0 to 30% acetonitrile mixed with a 0.1 M aqueous solution of ammonium acetate having a pH of 6). The fractions containing the polynucleotide are collected and lyophilized.

After treating the oligonucleotide with acetic acid (80% in water) at ambient temperature for 10 min, the 5' position of the polynucleotide is detritylated and the polynucleotide is then isolated following extraction with ether.

Subsequently, the nucleotide L, which was incorporated in the preceding step, is activated so as to obtain the polynucleotide diol 5'CGCACMCACGC3'(SEQ ID NO: 2), in which

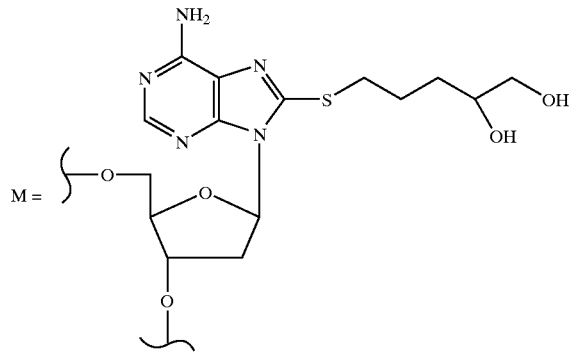

340 nmol of polynucleotide 5'CGCACLCACGC3' (SEQ ID NO: 1) are treated with a solution consisting of 170 µl of 0.02% osmium tetroxide, 2 µl of N-methylmorpholine-N-oxide and 2 µl of 3% $H_2O_2$. After incubating at ambient temperature overnight, the polynucleotide 5'CGCACM-CACGC3' (SEQ ID NO: 2) is purified by HPLC using the previously described conditions.

Finally the polynucleotide aldehyde 5'CGCACNCACGC3'(SEQ ID NO: 3), in which

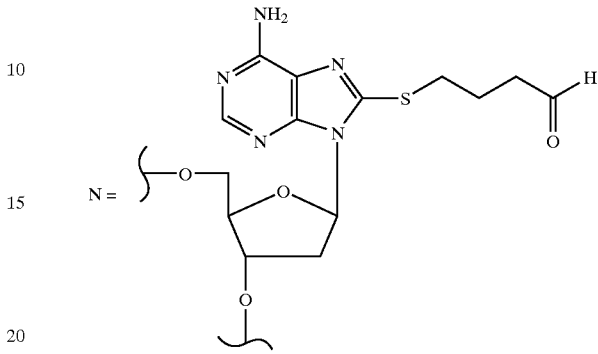

is obtained by adding, in the dark, 200 µl of 54 µM sodium metaperiodate to 200 µl of a 110 nM aqueous solution of oligonucleotide diol 5'CGCACMCACGC3'(SEQ ID NO: 2). After 15 min, the polynucleotide aldehyde 5'CGCACN-CACGC3' (SEQ ID NO: 3) is purified by HPLC (semi-preparative Macherey Nagel 10 mm×25 cm column; C18; 7 µm porosity; eluent: 20 min gradient of from 0 to 30% methanol mixed with a 20 mM aqueous solution of sodium dihydrogenphosphate at pH 6).

EXAMPLE 20

Labeling the Prefunctionalized Polynucleotide Obtained in Example 19

The labeling reaction is carried out using the reagent (40), which consists of a dansyl nucleus, as a functional fluorescent group, linked by way of a diethylene glycol chain to an oxyamino (nucleophilic) function. This reagent was prepared using the method described by D. BOUTURYN et al. in Tetrahedron, 1997, 53, 5485–5492.

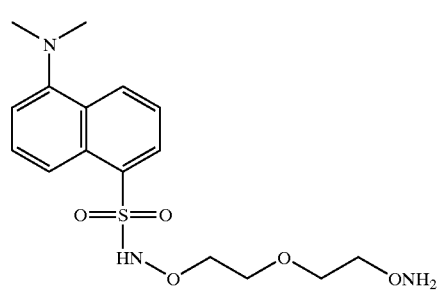

The labeling reaction is carried out in water in the presence of a slight excess of the reagent (40) (1.5 equivalent) in relation to the oligonucleotide. Monitoring the course of the reaction by HPLC indicates that the starting compounds disappear rapidly and that a new product corresponding to the functionalized polynucleotide (41) is formed. Analysis of the proton NMR spectrum furthermore confirms the attachment of the dansyl label.

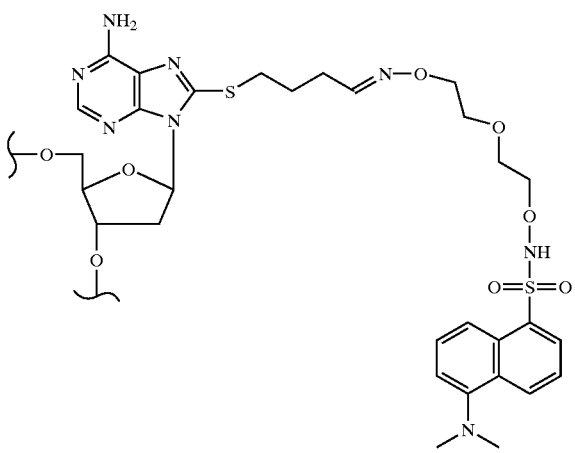

EXAMPLE 21

Enzymic Synthesis of a Prefunctionalized Polynucleotide by Means of Transcription Synthesis of the Prefunctionalized Nucleotide 2'-deoxy-8-(butanal)-thioadenosine-5'-triphosphate (43)

This synthesis is carried out using the 2'-deoxy-8-(pentenyl)thioadenosine (38) (see Example 19). The starting nucleotide (42) is obtained using the method described by J. LUDWIG and F. ECKSTEIN in J. Org. Chem., 1989, 54, 631–635.

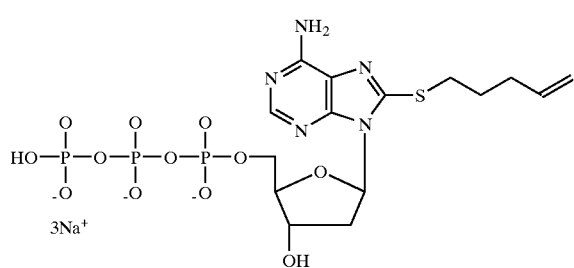

The oxidation steps which are required for obtaining the prefunctionalized nucleotide 43 are carried out as described in Example 19:

Enzymic incorporation of the prefunctionalized nucleotide (43):

a) Preparation of the DNA Template Carrying a Promoter

A PCR is performed on the gene HIVgag, which is carried in a linearized pGEM plasmid, using a standard primer and a primer which carries the sense sequence of a promoter for phage T7 RNA polymerase upstream of a standard primer sequence.

Sequences of the primers:
Standard primer (No. 4014)

5'-AGTGGGGGGACATCAAGCAGCCAT
GCAAA 3'     (SEQ ID NO: 4)

Promoter primer (No. 4003)

5'AATTCTAATACGACTCACTATAGGGTGC-
TATGTCACTTCCCCTTGGTTCTCTCA-3'    (SEQ ID NO: 5)

This results in a 158 base pair product, which is purified by extracting it with phenol/chloroform and passing it through microcon 30.

b) Transcription Reaction

The transcription reactions are performed in Eppendorf tubes, in a final volume of 25 µl, in a 40 mM tris/HCl buffer, pH 8.1, 20 mM $MgCl_2$, 5 mM dithiothreitol, 1 mm spermidine, 8% polyethylene glycol, 0.01% Triton x100, 50 µg/ml of bovine serum albumin/ml. The prefunctionalized nucleotide (43) and the four ribonucleotides (CTP, GTP, ATP and UTP) are added at concentrations of 1.33 mM and of 4 mM, for each of the ribonucleotides, respectively. The PCR template is added at a concentration of $10^9$ copies/µl, and the phage T7 RNA polymerase (patent application FR 97 04166) is added at a concentration of 1 u/µl. The reaction is incubated at 37° C. for 60 min. 0.5 u of DNAse 1/µl is added to the medium in order to destroy the DNA template. The incubation of the sample is continued at 37° C. for 15 min. The resulting RNAs are purified by being passed through Sephadex G50.

In parallel, a first control is performed by means of a reaction in which T7 RNA polymerase is not added. A second control is performed without any activated nucleotide, as a control for transcription having taken place.

The purified transcription products are labeled using the experimental method described in Example 2, and visualized under an ultraviolet light following electrophoretic migration in an agarose gel.

EXAMPLE 22

Synthesis of a Prefunctionalized Polynucleotide During an TMA Amplification Reaction In order to label the TMA amplification products intensively, prefunctionalized nucleotides 27a (CTP-(N4)-$C_6O_2$—$NH_2$), 27b (CTP-(N4)-C4—$NH_2$) and 32 (CTP-(N4)-$C_6$—$ONH_2$) are incorporated into the amplicons. Amplification reactions are conducted in parallel in the presence of a labeled nucleotide carrying a fluorescein, i.e. fluorescein-12-UTP (Boerhinger, ref. 1 427 857).

The incorporation of the prefunctionalized nucleotides 27a, 27b and 32, and, by way of comparison, Boerhinger's labeled nucleotide ref. 1 427 857, into the products of the TMA amplification reaction is tested using Gen-Probe amplified™ MTD2 (amplified Mycobacterium tuberculosis direct test) kits. This reaction amplifies a 136-base fragment of the mycobacterial 16S RNA. It uses four enzymic activities (DNA-dependent RNA polymerase, DNA-dependent DNA polymerase, RNA-dependent DNA polymerase and ribonuclease H) and two enzymes, T7 RNA polymerase and AMV reverse transcriptase. By means of recurrent reactions involving steps of transcription, reverse transcription and digestion of the RNA contained in the DNA:RNA double strands, which steps resemble an RNA virus replication cycle, this reaction enables a nucleic acid sequence which is recognized by two primers (a simple primer and a primer containing the T7 RNA polymerase promoter) to be amplified specifically. The amplification factor is very substantial (109) and the sensitivity is very good (from 1 to 10 copies). 90% of the resulting products consist of single-stranded RNAs and 10% consist of double-stranded DNAs.

Amplification reactions are carried out using $10^6$ copies of Mycobacterium tuberculosis 16S RNA. This target RNA is previously obtained and quantified by means of the following method: the 16S RNA gene is cloned into a plasmid under the control of a promoter. The 16S RNA is then obtained by in vitro transcription. This RNA is purified by extraction with phenol/chloroform and filtration through microcon 30™ (Amicon). It is assayed by its absorption at 260 nm.

The standard TMA reactions contain 4 mM of each of the natural rNTPs (ATP, CTP, GTP and UTP). For the purpose of incorporating the prefunctionalized nucleotides into the amplification products, the reaction is performed while including one of these modified nucleotides in the reaction buffer. The reaction is studied in the presence of different ratios between the concentrations of the modified nucleotide and the natural nucleotide, while at the same time ensuring that the total concentration of each nucleotide of the same series, whether modified or natural, is 4 mM. The ratios studied are 0%, 10%, 30%, 50% and 70% (except in the case of the fluorescein-UTP, which it was not possible to test at 70%). A negative control is carried out, with this negative control consisting of a reaction which comprises all the reagents, including the highest ratio of modified nucleotides employed (70 or 50%), apart from the enzymes (which are replaced by the buffer used for redissolving the lyophilized enzymes).

The amplification reactions are analyzed by electrophoresing 5 µl of reaction mixture on a denaturing polyacrylamide gel (6% acrylamide, 7 M urea, 1×TBE, bioRad electrophoresis apparatus, 170 volts, 45 minutes) and staining with ethidium bromide; this is then followed by Northern blotting. The nucleic acids are transferred to a membrane (nylon N, bioRad semi-dry transfer apparatus, 0.5×TBE, 25 V, 15 minutes) and hybridized with peroxidase-labeled nucleic acid probes which are specific for *Mycobacterium tuberculosis*:

(sequence: 5'-CGGGATGCATGTCTTGTGGT) (SEQ ID NO: 6)

(preincubation at 37° C. for 30 minutes in PEG, then incubation at 37° C. for 1 hour in the presence of PEG containing 0.1 ng of peroxidase probe/el). Visualization is by colorimetry (substrate, Diaminobenzidine, Sigma).

In the case of reactions containing the fluorescent nucleotide (fluorescein-12-UTP), the amplification products are also visualized on the gel, before staining with ethidium bromide, by excitation of the fluorescein on an ultraviolet table.

Following staining with ethidium bromide, large quantities of the expected amplification products are visualized in the case of all the reactions, including those which use the prefunctionalized nucleotides. Following Northern blotting, these products hybridize with the specific probe.

EXAMPLE 23

Analysis of the Incorporation Yields in the TMA Amplification Products

The ratio between the incorporated prefunctionalized nucleotide and the analogous natural nucleotide is determined in order to assess the prefunctionalization of the amplicons obtained in the presence of the prefunctionalized nucleotides 27a (CTP-(N4)-$C_6O_2$—$NH_2$) and 27b (CTP-(N4)-C4—$NH_2$) and, by way of comparison, in the presence of the labeled nucleotide fluorescein-12-UTP (Boerhinger, ref. 1 427 857).

The amplification products obtained on carrying out Example 22 are separated from the nucleotides which are in excess in the reaction by means of filtration through Microcon 30™ (from Amicon) and dissolved in 50 µl of water. In the case of the amplification in the presence of fluorescein-12-UTP, the purification is carried out on sephadex G50 (the fluorescein is absorbed on Microcon).

The absorption of the amplification products at 260 nm is then determined (the control without enzyme should have a very low concentration).

In the case of the amplification reactions which include the prefunctionalized nucleotides (and their controls), a step of digesting the nucleic acids down to the nucleoside stage is then carried out:

5 $10^{14}$ amplification product copies (approximately 35 µg) are diluted in a final volume of 86 µl of water (in the case of the control without enzyme, a volume is used which is equal to the largest sample 15 volume). 10 µl of 10×P1 nuclease buffer (300 mM CH3COONa buffer, pH 5.3, 1 mM ZnSO4) and 4 µl of P1 nuclease (Boerhinger, ref. 236225, 1 µg/µl, 0.3 u/µl) are added. The reaction mixture is incubated at 37° C. for 30 minutes. 12 µL of 10×alkaline phosphatase buffer (Boerhinger, ref. 1246283) and 1 µl of alkaline phosphatase (Boerhinger, ref. 713023, 1 U/µl) are then added and the incubation at 37° C. is continued for 15 minutes. The reaction is stopped in ice.

The nucleoside composition is then determined by high pressure liquid chromatographic analysis (HPLC, Beckman, Gold system) and by comparing with nucleoside standards (injection of 50 ng of each nucleoside). 20 µL of the digestion are injected onto a C18 (Ultrasphere) column which is heated at 45° C. The separation is carried out in 50 mM sodium phosphate buffer, pH 7, which includes a methanol gradient (after 10 minutes, passing within 15 minutes from 0% to 30% of 95% methanol). The peaks are visualized by absorption at 254 nm and the peak areas are calculated by integration.

The ratio between the area of the peak of the prefunctionalized nucleotide and that of its natural analog makes it possible to determine the incorporation yield, that is the ratio between the quantity of prefunctionalized nucleotide which is incorporated and the total quantity of nucleotide of the same series which is incorporated.

The control without enzyme should not give rise to a peak. This control testifies to the satisfactory efficacy of the step of removing the nucleotides which are in excess.

In the case of the amplification reactions which include fluorescein-UTP, the quantity of fluorescein nucleotide incorporated is measured by the intensity of the fluorescence: the intensity of the fluorescence of a standard range of fluorescein is read on a Perkin LS 50 spectrofluorimeter. The fluorescence intensity of the different amplification reactions is measured. The quantity of fluorescein incorporated is determined by comparing with the standard curve. The incorporation yield is calculated in relation to the amplicon concentration, which is measured by absorption at 260 nm.

The HPLC analysis makes it possible to separate the eight natural nucleosides as well as the three nucleosides which are analogous to the three prefunctionalized nucleotides which are tested.

The results, which are presented in the following table, demonstrate that all the prefunctionalized CTP nucleotides studied give an incorporation yield in the TMA amplification products which is superior to that for fluorescein-12-UTP, which is the labeled nucleotide which is conventionally employed.

| [Prefunctionalized nucl.]/ [natural nucl.] in % | 70 | 50 | 30 | 10 | 0 |
|---|---|---|---|---|---|
| 27a (CTP-(N4)-C6O2-NH2)/ natural CTP | 1/3 | 1/5 | 1/9 | 1/33 | 0 |
| 27b (CTP-(N4)-C4-NH2)/ natural CTP | 1/6 | 1/15 | 1/48 | ND | 0 |
| Boehringer, ref. 1 427 857 (fluorescein-12-UTP)/ natural CTP | ND | 1/30 | 1/45 | 1/200 | 0 |

ND: not determined. Nucl.: nucleotide

These results demonstrate that prefunctionalization of the CTP nucleotide permits an incorporation which is superior to that achieved by labeling with a fluorescein. The very good prefunctionalization of the amplicons makes it possible, after functionalization, to obtain a labeling which is more intense than that obtained with the fluorescein nucleotide.

An improved incorporation yield can similarly be achieved with other reactive functions, such as the oxyamino function of the nucleotide 32, which are introduced into the N4 position of the cytidine.

EXAMPLE 24

Analysis of the Impact of the Incorporation of the Prefunctionalized Nucleotides on TMA Sensitivity In order to study the sensitivity of TMA which includes incorporation of prefunctionalized nucleotides, the TMA was performed using decreasing quantities of the target (*Mycobacterium tuberculosis* 16S RNA, described in Example 22) (10,000, 1000, 100, 10 and 0 copies) in the presence of different ratios between the prefunctionalized nucleotide and its natural analog (100%, 70%, 50%, 30%, 10% and 0%). The same prefunctionalized nucleotides are tested, i.e. 27a (CTP-(N4)-$C_6O_2$—$NH_2$) and 27b (CTP-(N4)-$C_4$—$NH_2$).

The reaction products are studied, inter alia, by the method described in Example 22.

The reaction products are also analyzed in a semi-quantitative manner by means of ELOSA (PCT WO 92/19812) and comparison of the intensity of the signals with those of standard ranges.

The reactions which are performed in the presence of (a) prefunctionalized nucleotide(s) are analyzed by electrophoresis and staining, Northern blotting and ELOSA. The results obtained by ELOSA, which are representative of the different analytical methods employed, are shown in FIGS. 4 and 5. Whichever ever prefunctionalized nucleotide is employed (27a or 27b), it is possible to determine a concentration of prefunctionalized nucleotide(s) at which the sensitivity of the TMA reaction is not significantly affected even when the number of copies of the initial target is very low. As is more specifically evident from the attached FIG. 5, the nucleotide 27b is able to replace the natural nucleotide.

EXAMPLE 25

Labeling the Prefunctionalized Amplicons

The prefunctionalized amplicons which are obtained, in the presence of the prefunctionalized nucleotide 27b (CTP-(N4)-$C_4$—$NH_2$), by the method employed when carrying out Example 22 are labeled by means of a chemical coupling reaction between the nucleophilic function which is carried by the amplicons and supplied by the incorporated prefunctionalized nucleotides and an anti-reactive electrophilic function which has previously been coupled to fluorescein. The resulting labeling is compared with that obtained in the presence of the labeled nucleotide fluorescein-12-UTP (Boerhinger, ref. 1 427 857).

The amplicons are obtained by the method described in Example 22 using $10^6$ copies of the *Mycobacterium tuberculosis* 16S RNA target and in the presence of 50% of prefunctionalized nucleotide 27b.

The resulting amplicons are coupled to fluorescein-NHS (Boerhinger 8370042128), using the following method: 30 µl of TMA amplification products are mixed with 30 µl of 0.2 M carbonate, 0.15 M NaCl buffer, pH 8.8, and 40 µl (approximately 200 equivalents) of fluorescein NHS (3.5 mg/ml in DMSO). The labeling is analyzed after being shaken at ambient temperature for one hour.

The labeled amplicons (15 µl) are analyzed by gel electrophoresis as described in Example 22 and visualized under ultraviolet light, before and after staining with ethidium bromide. The profiles are compared with those obtained by labeling in the presence of 50% fluorescein-12-UTP.

The signals which are obtained without staining are more intense than those obtained by direct labeling with fluorescein. It is possible to obtain an equally good result, after coupling to the fluorophore 36, by using the oxyamino function as carried by the nucleotide 32. The reactivity of the oxyamino/aldehyde couple enables reduced coupling times to be achieved, as shown in Example 20.

What is claimed is:

1. Process for amplifying a sequence of a target nucleic acid which is present in a sample, according to which: at least the following are available: the sequence of a target nucleic acid, at least one oligonucleotide primer which is specific for the target sequence, one or more enzyme activities that amplify the sequence and nucleotides, and the target sequence is amplified under conditions which are suitable for the enzymic activity or activities, characterized in that, among the nucleotides available, at least one nucleotide is a prefunctionalized nucleotide which differs from the other nucleotides at least by the presence of at least one unprotected covalently reactive function which is arranged in at least one predetermined site of the base of said nucleotide and which is an electrophilic organic chemical function selected from the group consisting of aldehyde, activated ester, carboxylic acid, isothiocyanate, haloacyl derivatives and sulfonyl chloride functions or a nucleophilic organic chemical function selected from the group consisting of thiol, oxyamino, alkoxyamino, hydrazine and hydrazide functions, and in that, in addition the resulting prefunctionalized amplification product is reacted, directly or indirectly, with a reagent which contains a covalently anti-reactive function which is specific for the reactive function of the prefunctionalized nucleotide and a functional labeling group, with this latter being a non-protein, in order to obtain a functionalized amplification product, wherein one of (1) the reactive function of said prefunctionalized nucleotide and (2) the anti-reactive function of said reagent is an aldehyde function.

2. Process according to claim 1, characterized in that the functional labeling group of the reagent is a fluorescent chemical molecule.

3. Process according to claim 1, characterized in that the functional labeling group of the reagent is selected from fluorescein and dansyl.

4. Process according to claim 1, characterized in that the reactive function is the methoxyamino function.

5. Process according to claim 1, characterized in that the reactive function of the prefunctionalized nucleotide is attached to the base by way of a coupling arm.

6. Process according to claim 1, characterized in that the anti-reactive function of the reagent is selected from (i) the nucleophilic organic chemical functions, if the reactive function of the prefunctionalized nucleotide is an electrophilic function, and (ii) the electrophilic organic chemical functions, if the reactive function of the prefunctionalized nucleotide is a nucleophilic function.

7. Process according to claim 3, characterized in that the anti-reactive function of the reagent is the aldehyde function.

8. Process according to claim 6, characterized in that the anti-reactive function of the reagent is attached to the functional group by way of a coupling arm.

9. Process according to claim 5, characterized in that the coupling arm is selected from saturated or unsaturated hydrocarbon chains which may or may not be interrupted by amino, amido and oxy functions.

10. Process according to claim 7, characterized in that the aldehyde function is linked to the functional group by the coupling arm —NH—CS—NH—$(CH_2)_3$—, and in that the functional group of the reagent is fluorescein.

11. Process according to claim 1, characterized in that the target nucleic acid sequence is a DNA or RNA sequence and in that the enzymic activities comprise the RNA-dependent and/or DNA-dependent DNA polymerase activities.

12. Process for amplifying a sequence of a target nucleic acid which is present in a sample, according to which:

at least the following are available: the sequence of a target nucleic acid, at least one oligonucleotide primer which is specific for the target sequence, one or more enzyme activities that amplify the sequence and nucleotides, and the target sequence is amplified under conditions which are suitable for the enzymic activity or activities, wherein the target nucleic acid sequence is a DNA or RNA sequence and wherein the enzymic activities comprise the RNA-dependent and/or DNA-dependent DNA polymerase activities, characterized in that, among the nucleotides available, at least one nucleotide is a prefunctionalized nucleotide which differs from the other nucleotides at least by the presence of at least one unprotected covalently reactive function which is arranged in at least one predetermined site of the base of said nucleotide and which is an electrophilic organic chemical function selected from the group consisting of aldehyde, activated ester, carboxylic acid, isothiocyanate, haloacyl derivatives and sulfonyl chloride functions or a nucleophilic organic chemical function selected from the group consisting of thiol, oxyamino, alkoxyamino, hydrazine and hydrazide functions, and in that, in addition the resulting prefunctionalized amplification product is reacted, directly or indirectly, with a reagent which contains a covalently anti-reactive function which is specific for the reactive function of the prefunctionalized nucleotide and a functional labeling group, with this latter being a non-protein, in order to obtain a functionalized amplification product, and in that the enzymic activities additionally comprise ribonuclease H activity and DNA-dependent RNA polymerase activity.

13. Process according to claim 12, characterized in that the ribonuclease H and DNA polymerase enzymic activities are supplied by a single enzyme.

14. Process according to claim 12, characterized in that the ribonuclease H and DNA polymerase enzymic activities are each supplied by a different enzyme.

15. Process according to claim 1, characterized in that the base of the prefunctionalized nucleotide is derived from cytosine and contains, at least on the amino function in position 4 of the pyrimidine ring, at least one nucleophilic reactive function which is selected from the group consisting of —O—$NH_2$, alkoxyamino, —SH, hydrazine and hydrazide functions.

16. Process for amplifying a sequence of a target nucleic acid which is present in a sample, according to which:

at least the following are available: the sequence of a target nucleic acid, at least one oligonucleotide primer which is specific for the target sequence, one or more enzyme activities that amplify the sequence and nucleotides, and the target sequence is amplified under conditions which are suitable for the enzymic activity or activities, characterized in that, among the nucleotides available, at least one nucleotide is a prefunctionalized nucleotide which differs from the other nucleotides at least by the presence of at least one unprotected covalently reactive function which is arranged in at least one predetermined site of the base of said nucleotide, and which is an electrophilic organic chemical function selected from the group consisting of aldehyde, activated ester, carboxylic acid, isothiocyanate, haloacyl derivatives and sulfonyl chloride functions or a nucleophilic organic chemical function selected from the group consisting of thiol, oxyamino, alkoxyamino, hydrazine and hydrazide functions, and in that, in addition the resulting prefunctionalized amplification product is reacted, directly or indirectly, with a reagent which contains a covalently anti-reactive function which is specific for the reactive function of the prefunctionalized nucleotide and a functional labeling group, with this latter being a non-protein, in order to obtain a functionalized amplification product, and in that, in addition, the base of the prefunctionalized nucleotide is derived from cytosine and contains, at least on the amino function in position 4 of the pyrimidine ring, at least one nucleophilic reactive function that is the $-CH_2-O-NH_2$ function.

17. Process for amplifying a sequence of a target nucleic acid which is present in a sample, according to which:

at least the following are available: the sequence of a target nucleic acid, at least one oligonucleotide primer which is specific for the target sequence, one or more enzyme activities that amplify the sequence and nucleotides, and the target sequence is amplified under conditions which are suitable for the enzymic activity or activities, characterized in that, among the nucleotides available, at least one nucleotide is a prefunctionalized nucleotide which differs from the other nucleotides at least by the presence of at least one unprotected covalently reactive function which is arranged in at least one predetermined site of the base of said nucleotide, and which is an electrophilic organic chemical function selected from the group consisting of aldehyde, activated ester, carboxylic acid, isothiocyanate, haloacyl derivatives and sulfonyl chloride functions or a nucleophilic organic chemical function selected from the group consisting of thiol, oxyamino, alkoxyamino, hydrazine and hydrazide functions, and in that, in addition the resulting prefunctionalized amplification product is reacted, directly or indirectly, with a reagent which contains a covalently anti-reactive function which is specific for the reactive function of the prefunctionalized nucleotide and a functional labeling group, with this latter being a non-protein, in order to obtain a functionalized amplification product, and in that, in addition, the base of the prefunctionalized nucleotide is derived from cytosine and contains, at least on the amino function in position 4 of the pyrimidine ring, at least one nucleophilic reactive function which is selected from the group consisting of $-NH_2-O-NH_2$, alkoxyamino, $-SH$, hydrazine and hydrazide functions; and the reactive function is linked to the amino function in position 4 of the pyrimidine ring by way of a coupling arm which is selected from $-(CH_2-)n_1$ and $-(O-CH_2-)n_1$, in which $n_1$ is an integer of between 1 and 12; $[-(CH_2)_2-O-(CH_2)_2-]n_2$, $[-(CH_2)_2-O-(CH_2)_2-O-(CH_2)_2-]n_2$ and $[-CH_2-O-(CH_2)_2-]n_2$, in which $n_2$ is an integer of between 1 and 6, and $-NH-CH_2-O-(CH_2)_2-$.

18. Process according to claim 17, characterized in that the coupling arm is selected from $-CH_2-$, $(-CH_2-)_2$, $(-CH_2-)_3$, $(-CH_2-)_4$, $(-CH_2-)_6$, $-(CH_2)_2-O-(CH_2)_2-$, $-(CH_2)_2-O-(CH_2)_2-O-(CH_2)_2-$ and $-NH-CH_2-O-(CH_2)_2-$.

19. Process according to claim 17, characterized in that the coupling arm is $-(CH_2)_2-O-(CH_2)_2-O-(CH_2)_2-$.

20. Prefunctionalized nucleotide which is capable of being subjected to an enzymic treatment, the base of which is derived from cytosine and contains, at least on the amino function in position 4 of the ring of the pyrimidine base, at least one reactive function which consists of an alkoxyamino function which may or may not be linked to said amino function in said position 4 by way of a coupling arm.

21. Prefunctionalized nucleotide which is capable of being subjected to an enzymic treatment, the nucleobase of which is derived from cytosine and contains, at least on the amino function in position 4 of the ring of the pyrimidine base, at least one reactive function which consists of an amino function which is linked to said amino function in said position 4 by way of the coupling arm consisting of $[(CH_2)_2-O-(CH_2)_2-O-(CH_2)_2-]-(CH_2)_2-O-(CH_2)_2-O-(CH_2)_2-$.

22. Process according to claim 1, wherein the reactive function of said prefunctionalized nucleotide is an aldehyde function.

23. Process according to claim 1, wherein the anti-reactive function of said reagent is an aldehyde function.

* * * * *